(12) United States Patent
Morton et al.

(10) Patent No.: US 10,571,437 B2
(45) Date of Patent: Feb. 25, 2020

(54) TEMPERATURE COMPENSATION AND OPERATIONAL CONFIGURATION FOR BULK ACOUSTIC WAVE RESONATOR DEVICES

(71) Applicant: Qorvo US, Inc., Greensboro, NC (US)

(72) Inventors: Rick Morton, Bend, OR (US); Kevin McCarron, Bend, OR (US)

(73) Assignee: QORVO US, INC., Greensboro, NC (US)

(*) Notice: Subject to any disclaimer, the term of this patent is extended or adjusted under 35 U.S.C. 154(b) by 445 days.

(21) Appl. No.: 15/380,551

(22) Filed: Dec. 15, 2016

(65) Prior Publication Data

US 2017/0168026 A1    Jun. 15, 2017

Related U.S. Application Data

(60) Provisional application No. 62/267,497, filed on Dec. 15, 2015.

(51) Int. Cl.
   *G01N 29/28* (2006.01)
   *G01N 29/32* (2006.01)
   (Continued)

(52) U.S. Cl.
   CPC ...... *G01N 29/326* (2013.01); *B01L 3/502715* (2013.01); *B01L 3/502761* (2013.01);
   (Continued)

(58) Field of Classification Search
   CPC .............................................. G01N 2291/0426
   See application file for complete search history.

(56) References Cited

U.S. PATENT DOCUMENTS 3,766,041 A    10/1973   Wasa et al.
3,781,721 A    12/1973   Judd et al.
(Continued)

FOREIGN PATENT DOCUMENTS

JP          09-181369 A       7/1997
WO    WO 2006/101450 A1      9/2006
(Continued)

OTHER PUBLICATIONS

U.S. Appl. No. 62/646,208, filed Mar. 21, 2018, Deniz et al.
(Continued)

*Primary Examiner* — Lisa M Caputo
*Assistant Examiner* — Alex T Devito
(74) *Attorney, Agent, or Firm* — Mueting, Raasch & Gebhardt, P.A.

(57) ABSTRACT

Operational configuration and temperature compensation methods are provided for bulk acoustic wave (BAW) resonator devices suitable for operating with liquids. Temperature compensation methods dispense with a need for temperature sensing, instead utilizing a relationship between (i) change in frequency of a BAW resonator at a phase with adequate sensitivity and (ii) change in frequency of a phase that is correlated to temperature. Operational configuration methods include determination of an initial phase response of a BAW resonator in which temperature coefficient of frequency is zero, followed by comparison of sensitivity to a level of detection threshold for a phenomenon of interest.

17 Claims, 23 Drawing Sheets

(51) Int. Cl.
| | |
|---|---|
| *B01L 3/00* | (2006.01) |
| *G01N 29/24* | (2006.01) |
| *G01N 33/543* | (2006.01) |
| *H03H 3/013* | (2006.01) |
| *H03H 9/17* | (2006.01) |
| *G01N 29/02* | (2006.01) |
| *G01N 29/036* | (2006.01) |
| *H03H 9/02* | (2006.01) |

(52) U.S. Cl.
CPC ......... *G01N 29/022* (2013.01); *G01N 29/036* (2013.01); *G01N 29/2443* (2013.01); *G01N 33/54373* (2013.01); *H03H 3/013* (2013.01); *H03H 9/02102* (2013.01); *H03H 9/17* (2013.01); *B01L 2200/143* (2013.01); *B01L 2200/147* (2013.01); *B01L 2300/023* (2013.01); *B01L 2300/0627* (2013.01); *G01N 2291/0255* (2013.01); *G01N 2291/0426* (2013.01)

(56) References Cited

U.S. PATENT DOCUMENTS

| | | | |
|---|---|---|---|
| 4,320,320 | A | 3/1982 | Momosaki et al. |
| 4,640,756 | A | 2/1987 | Wang et al. |
| 4,719,383 | A | 1/1988 | Wang et al. |
| 5,473,216 | A | 12/1995 | Brosig et al. |
| 5,518,594 | A | 5/1996 | Marcquart et al. |
| 5,728,276 | A | 3/1998 | Katsuki et al. |
| 5,958,193 | A | 9/1999 | Brugge |
| 6,827,824 | B1 | 12/2004 | Blalock et al. |
| 6,831,525 | B1 * | 12/2004 | Beaudin ............... H03L 1/00 327/105 |
| 7,033,461 | B2 | 4/2006 | Tani et al. |
| 7,047,792 | B1 | 5/2006 | Bhethanabotla et al. |
| 7,468,608 | B2 | 12/2008 | Feucht et al. |
| 7,675,388 | B2 | 3/2010 | Cardona |
| 8,409,875 | B2 | 4/2013 | Johal et al. |
| 8,689,426 | B2 | 4/2014 | Thalmayr et al. |
| 2003/0159919 | A1 | 8/2003 | Fairbairn et al. |
| 2004/0216992 | A1 | 11/2004 | Ando et al. |
| 2005/0145477 | A1 | 7/2005 | Kaas et al. |
| 2005/0194545 | A1 | 9/2005 | Lee et al. |
| 2008/0197750 | A1 | 8/2008 | Katardjiev et al. |
| 2008/0247264 | A1 | 10/2008 | Gabl et al. |
| 2009/0134011 | A1 | 5/2009 | Rohrmann et al. |
| 2009/0246385 | A1 | 10/2009 | Felmetsger et al. |
| 2013/0033337 | A1 | 2/2013 | Nishihara et al. |
| 2014/0154697 | A1 * | 6/2014 | Johal ............... G01N 33/54373 435/7.1 |
| 2016/0099704 | A1 | 4/2016 | Jaakkola et al. |
| 2016/0197593 | A1 | 7/2016 | Hurwitz et al. |
| 2017/0110300 | A1 | 4/2017 | McCarron et al. |
| 2017/0111021 | A1 | 4/2017 | McCarron et al. |
| 2017/0111022 | A1 | 4/2017 | McCarron et al. |
| 2017/0111023 | A1 | 4/2017 | McCarron et al. |
| 2017/0111028 | A1 | 4/2017 | McCarron et al. |
| 2017/0168018 | A1 | 6/2017 | Morton et al. |

FOREIGN PATENT DOCUMENTS

| | | |
|---|---|---|
| WO | WO 2012/003994 A1 | 1/2012 |
| WO | PCT/US2016/056840 | 10/2016 |
| WO | PCT/US2016/056843 | 10/2016 |
| WO | PCT/US2016/066913 | 12/2016 |
| WO | WO 2017/066448 A1 | 4/2017 |
| WO | WO 2017/066449 A1 | 4/2017 |
| WO | WO 2017/106489 A3 | 6/2017 |

OTHER PUBLICATIONS

U.S. Appl. No. 62/646,212, filed Mar. 21, 2018, Deniz et al.
U.S. Appl. No. 62/646,213, filed Mar. 21, 2018, Deniz et al.
U.S. Appl. No. 15/293,063, filed Oct. 13, 2016, McCarron et al.
U.S. Appl. No. 15/293,071, filed Oct. 13, 2016, McCarron et al.
U.S. Appl. No. 15/293,082, filed Oct. 13, 2016, McCarron et al.
U.S. Appl. No. 15/293,091, filed Oct. 13, 2016, McCarron et al.
U.S. Appl. No. 15/293,108, filed Oct. 13, 2016, McCarron et al.
U.S. Appl. No. 15/360,462, filed Dec. 15, 2016, Morton et al.
International Patent Application No. PCT/US2016/066913, filed Dec. 15, 2016; International Search Report / Written Opinion dated Jul. 11, 2017; 22 pages.
International Patent Application No. PCT/US2016/066913, filed Dec. 15, 2016; International Preliminary Report on Patentability dated Jun. 28, 2018; 13 pages.
International Patent Application No. PCT/US2016/056840, filed Oct. 13, 2016; International Search Report / Written Opinion dated Jan. 20, 2017; 19 pages.
International Patent Application No. PCT/US2016/056840, filed Oct. 13, 2016; International Preliminary Report on Patentability dated Apr. 26, 2018; 14 pages.
International Patent Application No. PCT/US2016/056843, filed Oct. 13, 2016; International Search Report / Written Opinion dated Jan. 26, 2017; 18 pages.
International Patent Application No. PCT/US2016/056843, filed Oct. 13, 2016; International Preliminary Report on Patentability dated Apr. 26, 2018; 13 pages.
Chapter 2, Ferrari et al., "Overview of Acoustic-Wave Microsensors," in *Piezoelectric Transducers and Applications*. Vives (Ed.), Springer-Verlag Berling Heidelberg; 2008. Table of Contents and pp. 39-62.
Chapter 22, Yanagitani, "Shear Mode Piezoelectric Thin Film Resonators," in *Acoustic Waves—From Microdevices to Helioseismology*. Beghi (Ed.), InTech;Nov. 14, 2011. pp. 501-520.
Author Unknown, "Understanding Planar Magnetrons for PVD Coatings," Semicore Equipment, Inc., May 14, 2013, 4 pages, www.azonano.com/article.aspx?ArticleID=3454.
Bjurström, Johan, "Advanced Thin Film Electroacoustic Devices," Digital Comprehensive Summaries of Uppsala Dissertations from the Faculty of Science and Technology, 280, ISSN 1651-6214, 2007, 86 pages.
Bjurström, et al., "Design and Fabrication of Temperature Compensated Liquid FBAR Sensors," *2006 IEEE Ultrasonics Symposium*, Oct. 2-6, 2006, pp. 894-897.
Bjurström, et al., "Synthesis of Textured Thin Piezoelectric AlN Films With a Nonzero C-Axis Mean Tilt for the Fabrication of Shear Mode Resonators," IEEE Transactions on Ultrasonics, Ferroelectrics, and Frequency Control, vol. 53, No. 11, Nov. 2006, pp. 2095-2100.
Chang et al., "The influence of Mg doped ZnO thin films on the properties of Love wave sensors," May 28, 2008, *Sensors and Actuators B*, 132(1):290-295.
Chen et al., "Characteristics of Dual Mode AlN Thin Film Bulk Acoustic Wave Resonators," IEEE International Frequency Control Symposium [online]. May 19-21, 2008, published in: May 2008, *IEEE*, 609-14.
Chen et al., "The Liquid Sensor Using Thin Film Bulk Acoustic Resonator with C-Axis Tilted AlN Films," 2013, *Journal of Nanomaterials*, 2013:8.
Chen et al., "Temperature stability of ZnO-based Love wave biosensor with SiO2 buffer layer," Dec. 1, 2009, *Sensors and Actuators A*, 156(2):317-22.
Connolly, "Diffraction Basics, Part 2," Spring 2012, EPS400-002, *Introduction to X-Ray Powder Diffraction*, 12 pages.
Demiguel-Ramos, M. et al., "Induced Surface Roughness to Promote the Growth of Tilted-AlN Films for Shear Mode Resonators," 2013 Joint UFFC, EFTF and PFM Symposium Proceedings, 2013, IEEE, pp. 274-277.
Depla et al. "Sputter Deposition Process," 2010. *Handbook of Deposition Technologies for Films and Coatings: Science, Applications and Technology*, 253-96.
Fardeheb-Mammeri, A. et al., "Growth and characterization of c-axis included AlN films for shear wave devices," Semiconductor Science and Technology, vol. 23, Aug. 12, 2008, 7 pages.

(56) References Cited

OTHER PUBLICATIONS

Fardeheb-Mammeri, A. et al., "Growth of inclined c-axis AlN films in planar system for BAW devices," Journal of Electron Devices, vol. 5, 2007, pp. 132-137.

García-Gancedo, L. et al., "AlN-based BAW resonators with CNT electrodes for gravimetric biosensing," Sensors and Actuators B: Chemical, vol. 160, No. 1, Dec. 15, 2011, pp. 1386-1393.

García-Gancedo, L., et al., "Dual-Mode Thin Film Bulk Acoustic Wave Resonators for Parallel Sensing of Temperature and Mass Loading," Biosensors and Bioelectronics, vol. 38, No. 1, Oct.-Dec. 2012, pp. 369-374.

Iriarte, Gonzalo F. et al., "Synthesis of C-Axis-Oriented AlN Thin Films on High-Conducting Layers: Al, Mo, Ti, TiN, and Ni," IEEE Transactions on Ultrasonics, Ferroelectrics, and Frequency Control, vol. 52, No. 7, Jul. 2005, pp. 1170-1174.

Jamneala et al. "Modified Mason Model for Bulk Acoustic Wave Resonators," Sep. 2008, IEEE Transactions on Ultrasonics, Ferroelectrics, and Frequency Control, 55(9):2025-29.

Kobayashi, "X-ray thin film measurement techniques: IV. In-plan XRD measurements," 2010, The Rigaku Journal, 26(1):3-11.

Koskenvuori et al., "Temperature Measurement and Compensation Based on Two Vibrating Modes of a Bulk Acoustic Mode Microresonator," MEMS 2008, Tucson, Arizona, Jan. 13-17, 2008, pp. 78-81.

Lakin, "Modeling of Thin Film Resonators and Filters," 1992, IEEE MTT-S Microwave Symposium Digest, pp. 149-152.

Lee et al., "Microfluidic Mixing: A Review," May 18, 2011, International Journal of Molecular Sciences, 12:3263-87.

Montagut, Yeison et al. "QCM Technology in Biosensors," Biosensors—Emerging Materials and Applications, Chapter 9, 2011, INTECH Open Access Publisher, pp. 153-178.

Moreria, Milena et al., "Synthesis of c-tilted AlN films with a good tilt and thickness uniformity," 2011 IEEE International Ultrasonics Symposium Proceedings, 2011, pp. 1238-1241.

Moreira, Milena De Albuquerque, "Synthesis of Thin Piezoelectric AlN Films in View of Sensors and Telecom Applications," Digital Comprehensive Summaries of Uppsala Dissertations from the Faculty of Science and Technology, 1160, ISSN 1651-6214, 2014, 84 pages.

Qin et al., "Analytical Study of Dual-Mode Thin Film Bulk Acoustic Resonators (FBARs) Based on ZnO and AlN Films with Tilted c-Axis Orientation," Aug. 2010, IEEE Trans. UFFC, 57(8):1840-53.

Stan, G. E. et al., "Tilt c Axis Crystallite Growth of Aluminium Nitride Films by Reactive RF-Magnetron Sputtering," Digest Journal of Nanomaterials and Biostructures, vol. 7, No. 1, Jan.-Mar. 2012, pp. 41-50.

Suzuki, Masashi et al., "C-axis parallel oriented AlN film resonator fabricated by ion-beam assisted RF magnetron sputtering," 2011 IEEE International Ultrasonics Symposium Proceedings, 2011, pp. 1230-1233.

Thornton, "Influence of apparatus geometry and deposition conditions on the structure and topography of thick sputtered coatings," 1974, J. Vac. Sci. Technology, A 11:666.

Waite, Matthew M. et al., "Sputtering Sources," 50 Years of Vacuum Coating Technology and the growth of the Society of Vacuum Coaters, Chapter 15, 2007, Society of Vacuum Coaters, Spring Bulletin, 2010, pp. 42-50.

Wang, J.S. et al., "Sputtered C-Axis Inclined Piezoelectric Films and Shear Wave Resonators," IEEE 37th Annual Symposium on Frequency Control, 1983, IEEE, pp. 144-150.

Yanagitani, T. et al., "Pure-shear mode BAW resonators consisting of (11-20) textured ZnO films," Acoustics 08 Paris, 2008, pp. 4987-4992.

Ye, et al. "Photoreactivity of Alkysiloxane Self-Assembled Monolayers on Silicon Oxide Surfaces," Langmuir, vol. 17, No. 15, Jun. 21, 2001, pp. 4497-4500.

Yu, et al., "Ultra Temperature-Stable Bulk-Acoustic-Wave Resonators with $SiO_2$ Compensation Layer," Oct. 2007, IEEE Transactions on Ultrasonics, Ferroelectrics, and Frequency Control, 54(10):2102-2109.

Zhang, X et al. "Excimer laser ablation of thin gold films on quartz crustal microbalance at various argon background pressures," Applied Physics A, vol. 64, No. 6, Jun. 1997 pp. 545-552.

Zhou, Yan et al. "Interfacial Structures and Properties of Organize Materials for Biosensors: An Overview," Sensors, vol. 12 Nov. 6, 2012, pp. 15039-15062.

Qorvo US, Inc., "Summary of Sales Activity of Predecessor to Applicant Concerning Tilted C-Axis Aluminum Nitride Products," Unpublished, Jan. 10, 2017, 1 page.

Corso, Christopher et al., "Development of a Simple Inexpensive Bulk Acoustic Wave (BAW) Nanosensor for Cancer Biomarkers: Detection of Secreted Sonic Hedgehog from Prostate Cancer Cells," Abstract #8866, Winship Cancer Institute, Emory University, Georgia Institute of Technology, Oct. 2012, 1 page.

Link, Mathias, "Study and realization of shear wave mode solidly mounted film bulk acoustic resonators (FBAR) made of c-axis inclined zinc oxide (ZnO) thin films: application as gravimetric sensors in liquid environments," Université Henri Poincaré—Nancy I, Thesis, Sep. 14, 2006, 225 pages.

Milyutin, Evgeny, "Theoretical and Experimental Study of Piezoelectric Modulated AlN Thin Films for Shear Mode BAW Resonators," EPFL, Thesis No. 5113, Nov. 4, 2011, 109 pages.

Munir, Farasat, "A Fast, Scalable Acoustic Resonator-Based Biosensor Array System for Simultaneous Detection of Multiple Biomarkers," Thesis, Georgia Institute of Technology, Dec. 2012, 160 pages.

Virschl, Martin et al., "CMOS-Integrated Film Bulk Acoustic Resonators for Label-Free Biosensing," Sensors, vol. 10, No. 5, Apr. 27, 2010, pp. 4180-4193.

Petit, D., et al., "Temperature Compensated BAW Resonator and Its Integrated Thermistor for a 2.5 GHz Electrical Thermally Compensated Oscillator," IEEE Radio Frequency Integrated Circuits Symposium, Jun. 7-9, 2009, pp. 339-342.

Pierce, Daniel E. et al., "A Temperature Insensitive Quartz Microbalance," IEEE Transactions on Ultrasonics, Ferroelectrics, and Frequency Control, vol. 45, No. 5, Sep. 1998, pp. 1238-1245.

Rabus, D. et al., "A high sensitivity open loop electronics for gravimetric acoustic wave-based sensors," IEEE Transactions on Ultrasonics Ferroelectrics and Frequency Control, vol. 60, No. 6, Mar. 11, 2013, 14 pages.

Smith, James H. et al., "Self-Consistent Temperature Compensation for Resonant Sensors With Application to Quartz Bulk Acoustic Wave Chemical Sensors," 8th International Conference on Solid-State Sensors and Actuators, Jun. 25-29, 1995, IEEE, 6 pages.

Sebastian, Chapter 2, "Dielectric Materials for Wireless Communication" in Measurement of Microwave Dielectric Properties and Factors Affecting Them, 2008. pp. 11-47.

\* cited by examiner

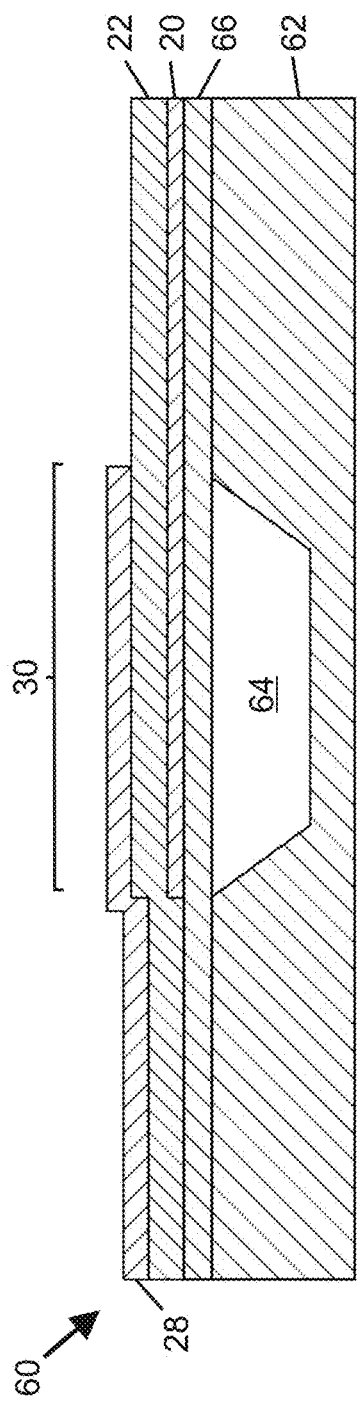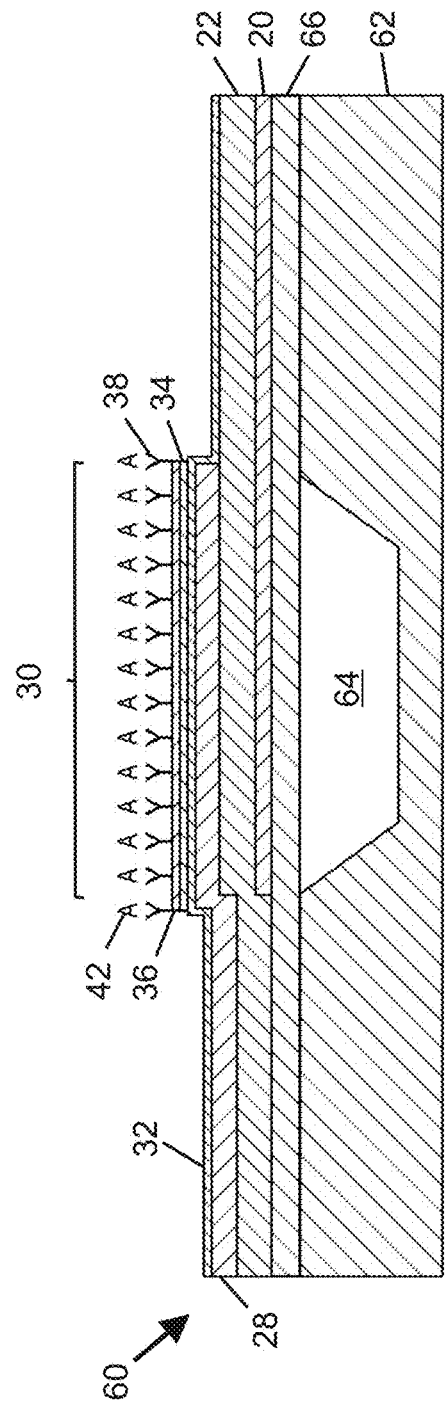
FIG. 5A
FIG. 5B

| Phase Crossing (Degrees) | Frequency Shift (kHz) | Sensitivity (kHz/% Glycerine) |
|---|---|---|
| −75 | 4.1 | 41 |
| −80 | −0.3 | −3 |
| −85 | −3.6 | −36 |
| −90 | −4.8 | −48 |
| −100 | −6.9 | −69 |
| −110 | −8.5 | −85 |
| −120 | −10.4 | −104 |
| −130 | −15.1 | −151 |
| −135 | −19.9 | −199 |

| Phase Crossing (°) | β |
|---|---|
| −75 | 1.67 |
| −85 | 0.73 |
| −90 | 0.57 |
| −100 | 0.31 |
| −110 | 0.16 |
| −120 | −0.14 |
| −130 | −0.30 |
| −135 | −0.61 |

*FIG. 21*

TEMPERATURE COMPENSATION AND OPERATIONAL CONFIGURATION FOR BULK ACOUSTIC WAVE RESONATOR DEVICES

STATEMENT OF RELATED APPLICATIONS

This application claims the benefit of provisional patent application Ser. No. 62/267,497, filed Dec. 15, 2015, the disclosure of which is hereby incorporated herein by reference in its entirety.

TECHNICAL FIELD

The present disclosure relates to bulk acoustic wave resonator devices and fluidic devices incorporating bulk acoustic wave resonators, including fluidic devices and related systems suitable for biosensing or biochemical sensing applications.

BACKGROUND

A biosensor (or biological sensor) is an analytical device including a biological element and a transducer that converts a biological response into an electrical signal. Certain biosensors involve a selective biochemical reaction between a specific binding material (e.g., an antibody, a receptor, a ligand, etc.) and a target species (e.g., molecule, protein, DNA, virus, bacteria, etc.), and the product of this highly specific reaction is converted into a measurable quantity by a transducer. Other sensors may utilize a non-specific binding material capable of binding multiple types or classes of molecules or other moieties that may be present in a sample. The term "functionalization material" may be used herein to generally relate to both specific and non-specific binding materials. Transduction methods used with biosensors may be based on various principles, such as electrochemical, optical, electrical, acoustic, etc. Among these, acoustic transduction offers a number of potential advantages, such as being real time, label-free, and low cost, as well as exhibiting high sensitivity.

An acoustic wave device employs an acoustic wave that propagates through or on the surface of a specific binding material, whereby any changes to the characteristics of the propagation path affect the velocity and/or amplitude of the wave. Acoustic wave devices are commonly fabricated by micro-electro-mechanical systems (MEMS) fabrication techniques, owing to the need to provide microscale features suitable for facilitating high-frequency operation. Presence of functionalization material on or over an active region of an acoustic wave device permits an analyte to be bound to the functionalization material, thereby altering the mass being vibrated by the acoustic wave and altering the wave propagation characteristics (e.g., velocity, thereby altering resonance frequency). Changes in velocity can be monitored by measuring the frequency, amplitude-magnitude, and/or phase characteristics of the acoustic wave device and can be correlated to a physical quantity being measured.

In the case of a piezoelectric crystal resonator, an acoustic wave may embody a bulk acoustic wave (BAW) propagating through the interior (or "bulk") of a piezoelectric material. BAW resonator devices typically involve transduction of an acoustic wave using electrodes arranged on opposing top and bottom surfaces of a piezoelectric material. In a BAW resonator device, three wave modes can propagate, namely, one longitudinal mode (embodying longitudinal waves, also called compressional/extensional waves), and two shear modes (embodying shear waves, also called transverse waves), with longitudinal and shear modes respectively identifying vibrations where particle motion is parallel to or perpendicular to the direction of wave propagation. The longitudinal mode is characterized by compression and elongation in the direction of the propagation, whereas the shear modes consist of motion perpendicular to the direction of propagation with no local change of volume. Longitudinal and shear modes propagate at different velocities. In practice, these modes are not necessarily pure modes as the particle vibration, or polarization, is neither purely parallel nor purely perpendicular to the propagation direction. The propagation characteristics of the respective modes depend on the material properties and propagation direction respective to the c-axis orientations. The ability to create shear displacements is beneficial for operation of acoustic wave devices with fluids because shear waves do not impart significant energy into fluids.

Although the preceding discussion has been focused primarily on biosensing and biochemical sensing applications in which mass is subject to being bound over an active region, BAW resonator devices may be used to detect various phenomena of interest, such as pressure in an environment containing an active region of a BAW resonator, density of a fluid medium arranged on or over an active region of a BAW resonator, and viscosity of a fluid medium arranged on or over an active region of a BAW resonator. Under an initial (e.g., no load) condition, an active region of a BAW resonator receiving an AC signal will vibrate at a natural resonance frequency. In exposure to a second condition (e.g., mass binding, pressure change, fluid viscosity change, fluid density change, etc.) that perturbs the active region (whether in a reversible or irreversible manner), the resonance frequency will shift, and a phenomenon of interest may be detected.

Temperature compensation in bulk acoustic wave (BAW) based liquid environment sensing applications is essential for creating a high-performance sensor with good sensitivity and a low limit of detection. This is because resonant sensors generally exhibit temperature sensitivities greater than the sensitivity of the phenomenon they are trying to detect. BAW-based sensor devices can operate in the 1-10 GHz frequency range with temperature coefficients of frequency (TCF) in the −20 to 0 ppm/° C. range for most aluminum nitride (AlN) based devices. For a device operating at 5 GHz with a −20 ppm/° C. TCF, a one degree change in temperature will bring about a −100 kHz shift in frequency. Often the frequency shift that is measured in liquid-based sensing systems is on the order of kilohertz, so temperature drift is clearly an issue that needs to be properly taken into account.

Temperature drift can be taken into account by three main methods: (1) maintaining a stable temperature environment in which the sensor will operate, (2) fabricating a device with 0 TCF at the frequency of interest, or (3) processing obtained sensor response data using methods that aim to subtract the temperature effects. The first and second methods can be hard to realize in practice, as a device with a TCF value even as low as 1 ppm/° C. TCF will experience a 5 kHz shift due to a 1 degree change in temperature when operated at 5 GHz. The third method traditionally requires either an independent measurement of the device temperature to be able to subtract the effect of temperature changes, or a separate reference device fabricated in proximity to the sensor. Use of a temperature sensor for temperature compensation, however, has multiple drawbacks, including: (i) introduction of an independent source of signal noise, thereby negatively affecting a net signal-to-noise ratio of a temperature compensated signal, (ii) introduction of a source of baseline drift; and (iii) increased cost and complexity of temperature measurement and data acquisition hardware.

Additionally, it may be challenging to select a phase crossing of a BAW resonator to be monitored as a function of time, particularly since a phase exhibiting maximum sensitivity may not necessarily provide an optimal signal in an environment in which temperature is changing.

Accordingly, there is a need for methods and systems providing improved temperature compensation and/or improved operational configuration of bulk acoustic wave resonators suitable for operation in the presence of liquid for biosensing or biochemical sensing applications in which temperature is subject to change, and that overcome limitations associated with conventional systems and methods.

SUMMARY

The present disclosure provides methods for operational configuration and for temperature compensation for bulk acoustic wave (BAW) resonator devices suitable for operating with liquids in applications in which temperature is subject to change. Temperature compensation methods provided herein do not require sensing of temperature of a resonator device or obtaining a reference temperature. Instead, a phase angle at which temperature and phase are correlated is determined. A relationship is determined between the frequency shift at this phase angle and the frequency shift at the phase angle where the measurement will be conducted. Upon obtaining a raw S-parameter response signal from a BAW resonator, such signal may be temperature corrected using a relationship between (i) change in frequency of the BAW resonator at a phase with adequate sensitivity and (ii) change in frequency of a phase that is correlated to temperature. Additionally, Applicant has found that the selection of phase crossing to be monitored determines the sensitivity of a BAW resonator. Operational configuration methods provided herein include determination of an initial phase response of a BAW resonator in which temperature coefficient of frequency is zero. If this initial phase provides sensitivity that is greater than or equal to a limit of detection threshold for a phenomenon of interest, then the initial phase is selected for monitoring; otherwise, one or more alternative phases are compared to the limit of detection threshold for the phenomenon of interest until a phase providing suitably high sensitivity is selected, preferably to enable operation of the BAW resonator with maximum sensitivity and minimum temperature dependence. Optionally, operational configuration method steps as disclosed herein may be used in combination with temperature compensation method steps as disclosed herein.

In one aspect, the disclosure relates to a sensing method utilizing a bulk acoustic wave (BAW) resonator, involving temperature correction that does not require use of a temperature signal, with the method including multiple steps. One step includes applying an AC signal to the BAW resonator. Another step includes obtaining a raw S-parameter response signal from the BAW resonator, wherein the raw S-parameter response signal includes a first phase of measurement and a second phase of measurement. Yet another step includes temperature correcting the raw S-parameter response signal, wherein the temperature correction utilizes a functional relationship between (i) a first change in frequency of the BAW resonator at the first phase of measurement and (ii) a second change in frequency of the BAW resonator at the second phase of measurement, wherein the second change in frequency is correlated to temperature.

In certain embodiments of the sensing method, each of the first phase of measurement and the second phase of measurement comprises at least one of: phase of S11, phase of admittance, or phase of impedance.

In certain embodiments of the sensing method, the functional relationship comprises a ratio between (i) the first change in frequency of the BAW resonator at the first phase of measurement and (ii) the second change in frequency of the BAW resonator at the second phase of measurement.

In certain embodiments of the sensing method, the first phase of measurement corresponds to a frequency of response of the BAW resonator in which a temperature coefficient of frequency is positive, and the second phase of measurement corresponds to a frequency of response of the BAW resonator in which the temperature coefficient of frequency is negative.

In certain embodiments of the sensing method, the first phase of measurement is performed at a phase angle where the BAW resonator exhibits non-zero sensitivity to a phenomenon of interest.

In certain embodiments of the sensing method, the phenomenon of interest comprises at least one of: pressure in an environment containing an active region of the BAW resonator, binding of mass on or over an active region of the BAW resonator, density of a fluid medium arranged on or over an active region of the BAW resonator, or viscosity of a fluid medium arranged on or over an active region of the BAW resonator.

In certain embodiments, the sensing method further comprises supplying a fluid containing an analyte to a fluidic passage of a fluidic device containing an active region of the BAW resonator, wherein at least one functionalization material is arranged over at least a portion of the active region, and said supplying is configured to cause at least some of the analyte to bind to the at least one functionalization material.

In certain embodiments of the sensing method, the applying of the AC signal to the BAW resonator induces a bulk acoustic wave in the active region, and the obtaining of the raw S-parameter response signal is used to sense at least one of an amplitude-magnitude property, a frequency property, or a phase property of the BAW resonator to indicate at least one of presence or quantity of target species bound to the at least one functionalization material.

In certain embodiments of the sensing method, the BAW resonator comprises a piezoelectric material including a c-axis having an orientation distribution that is predominantly non-parallel to normal of a face of a substrate, and the applying of the AC signal to the BAW resonator induces a bulk acoustic wave having dominant shear response in the active region. The term "dominant shear response" as used herein refers to motion with a greater shear (e.g., horizontal) magnitude than longitudinal (e.g., vertical) magnitude.

In another aspect, the disclosure relates to a method for configuring operation of a BAW resonator, with the method including multiple steps. One step includes determining an initial phase in a response of the BAW resonator where temperature coefficient of frequency is substantially equal to zero.

Another step includes comparing (i) sensitivity of the BAW resonator for a phenomenon of interest at the initial phase to (ii) a limit of detection threshold for the phenomenon of interest for the BAW resonator. Yet another step includes selecting a phase of the BAW resonator to be monitored as a function of time, wherein said selecting of a phase is responsive to comparison of sensitivity of the BAW resonator to the phenomenon of interest at at least one phase to the limit of detection threshold. Preferably, the foregoing method permits operation with maximum sensitivity and minimum temperature dependence for a phenomenon of interest to be detected.

In certain embodiments, the foregoing method further comprises determining sensitivity of the BAW resonator for the phenomenon of interest at the initial phase prior to the comparing of sensitivity of the BAW resonator.

In certain embodiments, if sensitivity of the BAW resonator for the phenomenon of interest at the initial phase is greater than or equal to the limit of detection threshold for the phenomenon of interest, then the selecting of a phase of the BAW resonator comprises selecting the initial phase.

In certain embodiments, if sensitivity of the BAW resonator at the initial phase is less than the limit of detection threshold, then the method further comprises: determining sensitivity of the BAW resonator for the phenomenon of interest at an alternative phase; and comparing sensitivity of the BAW resonator for the phenomenon of interest at the alternative phase to the limit of detection threshold for the phenomenon of interest for the BAW resonator. If sensitivity of the BAW resonator at the alternative phase is greater than or equal to the limit of detection threshold, then the selecting of a phase of the BAW resonator comprises selecting the alternative phase. In certain embodiments, the alternative phase comprises a more negative angle than the initial phase.

In certain embodiments, the phenomenon of interest comprises pressure in an environment containing an active region of the BAW resonator. In certain embodiments, the phenomenon of interest comprises binding of mass to an active region of the BAW resonator. In certain embodiments, the phenomenon of interest comprises density of a fluid medium contacting an active region of the BAW resonator. In certain embodiments, the phenomenon of interest comprises viscosity of a fluid medium contacting an active region of the BAW resonator.

In certain embodiments, the method further comprises configuring a temperature compensation scheme to be applied to at least one output signal of the BAW resonator when the alternative phase of the BAW resonator is monitored as a function of time. In certain embodiments, such a temperature compensation scheme includes: obtaining a raw S-parameter response signal from the BAW resonator, wherein the raw S-parameter response signal includes a first phase of measurement and a second phase of measurement; and temperature correcting the raw S-parameter response signal, wherein the temperature correction utilizes a functional relationship between (i) a first change in frequency of the BAW resonator at the first phase of measurement and (ii) a second change in frequency of the BAW resonator at the second phase of measurement, wherein the second change in frequency is correlated to temperature, and wherein the temperature correction does not require use of a temperature signal.

In certain embodiments, at least one of (i) the determining of the initial phase in the response of the BAW resonator where temperature coefficient of frequency is substantially equal to zero or (ii) the determining of sensitivity of the BAW resonator at the initial phase, is performed empirically utilizing a BAW resonator.

In certain embodiments, the method further comprises: selecting an AC signal to be supplied to the BAW resonator; and configuring a memory to store and/or display an output signal comprising frequency data at a phase of the BAW resonator selected to be monitored.

In certain embodiments, the method further comprises supplying a fluid containing an analyte to a fluidic passage of a fluidic device containing an active region of the BAW resonator, wherein at least one functionalization material is arranged over at least a portion of the active region, and said supplying is configured to cause at least some of the analyte to bind to the at least one functionalization material.

In certain embodiments, the BAW resonator comprises a piezoelectric material including a c-axis having an orientation distribution that is predominantly non-parallel to normal of a face of a substrate.

In certain embodiments, the method further comprises supplying an AC signal to the BAW resonator to induce a bulk acoustic wave in the active region, and sensing at least one of an amplitude-magnitude property, a frequency property, or a phase property of the BAW resonator to indicate at least one of presence or quantity of analyte bound to the at least one functionalization material.

In another aspect, the disclosure relates to a non-transitory computer readable medium containing program instructions for execution by at least one processor of a computer system to cause the computer system to perform steps of a method as disclosed herein. In one example, the steps include: determining, by the computer system, an initial phase in a response of a BAW resonator where temperature coefficient of frequency is substantially equal to zero; comparing, by the computer system, (i) sensitivity of the BAW resonator for a phenomenon of interest at the initial phase to (ii) a limit of detection threshold for the phenomenon of interest for the BAW resonator; and selecting, by the computer system, a phase of the BAW resonator to be monitored as a function of time, wherein said selecting of a phase is responsive to comparison of sensitivity of the BAW resonator for the phenomenon of interest at at least one phase to the limit of detection threshold. In another example, the steps include: obtaining, by the computer system, a raw S-parameter response signal from a BAW resonator generated upon application of an AC signal to the BAW resonator, wherein the raw S-parameter response signal includes a first phase of measurement and a second phase of measurement; and temperature correcting the raw S-parameter response signal, wherein the temperature correction utilizes a functional relationship between (i) a first change in frequency of the BAW resonator at the first phase of measurement and (ii) a second change in frequency of the BAW resonator at the second phase of measurement, wherein the second change in frequency is correlated to temperature, and wherein the temperature correction does not require use of a temperature signal.

In another aspect, any one or more aspects or features of one or more embodiments may be combined with aspects or features of one or more other embodiments for additional advantage, unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

FIG. 5A is a schematic cross-sectional view of a film bulk acoustic wave resonator (FBAR) structure usable in devices according to certain embodiments, with the FBAR structure including an inclined c-axis hexagonal crystal structure piezoelectric material, a substrate defining a cavity optionally covered by a support layer, and an active region registered with the cavity, with a portion of the piezoelectric material arranged between overlapping portions of a top side electrode and a bottom side electrode.

FIG. 5B is a schematic cross-sectional view of the FBAR structure according to FIG. 5A, following addition of a hermeticity layer, an interface layer, a self-assembled monolayer (SAM), and a functionalization (e.g., specific binding) material over at least portions of the FBAR structure.

FIG. 21 is a table of β values for multiple investigated phase crossing values.

DETAILED DESCRIPTION

Figure 1:
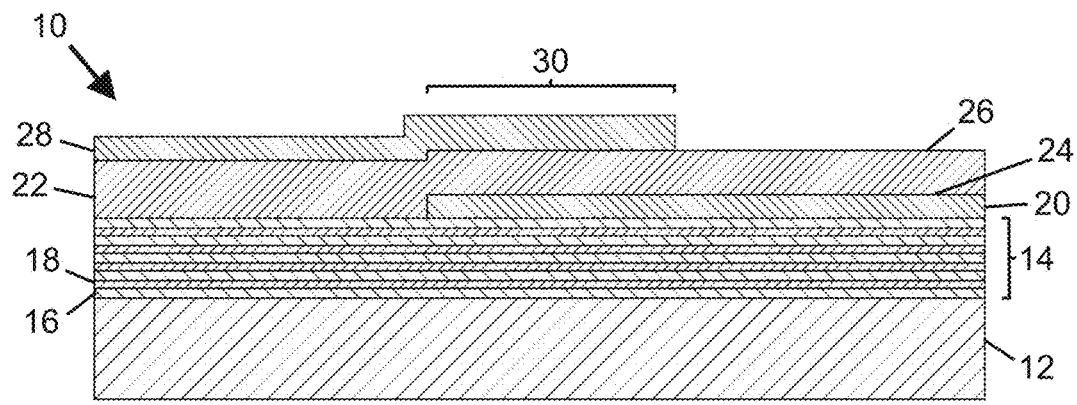
FIG. 1 is a schematic cross-sectional view of a portion of a bulk acoustic wave (BAW) MEMS resonator device usable for fabricating fluidic devices according to embodiments disclosed herein, including an active region with a piezoelectric material arranged between overlapping portions of a top side electrode and a bottom side electrode.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

The present disclosure provides methods for operational configuration and for temperature compensation for bulk acoustic wave (BAW) resonator devices suitable for operating with liquids in applications in which temperature is subject to change. Temperature compensation methods disclosed herein dispense with the need for sensing of temperature of a BAW resonator or obtaining a reference temperature. Rather, a phase angle is determined in which temperature is correlated with a particular phase angle, and a relationship is determined between the frequency shift at this phase angle and the frequency shift at the phase angle where the measurement will be conducted. A raw S-parameter response signal from a BAW resonator may be temperature corrected using a relationship between (i) change in frequency of the BAW resonator at a phase with adequate sensitivity and (ii) change in frequency of a phase that is correlated to temperature. The methods described herein may be used for any swept frequency sensor readback methodologies.

Various methods disclosed herein are applicable to BAW resonators capable of providing sensing utility in exposure to fluids (e.g., liquids). For example, a BAW resonator may be incorporated into a fluidic device arranged to receive a liquid, and/or may be exposed to a liquid environment. BAW resonators include active regions that are highly sensitive to changes in mass and/or fluid conditions, and may be used to sense various phenomena of interest, such as (but not limited to): binding of mass (e.g., chemical or biological species) to a surface overlying an active region of a BAW resonator, pressure in an environment containing an active region of a BAW resonator, density of a fluid medium arranged on or over an active region of a BAW resonator, and viscosity of a fluid medium arranged on or over an active region of a BAW resonator. Under the application of an AC signal to electrodes of a BAW resonator configured to produce a dominant shear mode response in the active region, the active region vibrates at a resonant frequency. Alteration of an environment of the BAW resonator may perturb the active region, causing the resonant frequency to shift, and thereby permitting a phenomenon of interest to be detected.

Since binding of mass over an active region of a BAW resonator may be difficult to reverse, various experiments performed by Applicant to develop this disclosure involved alteration of composition (and therefore density and viscosity properties) of liquid contacting an active region of a BAW resonator, due to its ease of reversibility. It is to be appreciated that experimental results discussed herein in support of Applicant's novel temperature compensation and operational configuration methods are applicable to any suitable phenomena of interest, including but not limited to mass loading (e.g., as used in biosensing and biochemical sensing devices).

Before describing Applicant's novel temperature compensation and operational configuration methods in detail, exemplary bulk acoustic wave MEMS resonator devices, associated layers useful for providing biochemical sensing utility, fluidic devices incorporating BAW MEMS resonator devices, electrical components of a sensing system incorporating a BAW MEMS resonator device, and a liquid supply switching sensor test apparatus used to perform experiments and generate data supporting Applicant's disclosure will be introduced.

Exemplary Bulk Acoustic Wave MEMS Resonator Devices

FIG. 1 is a schematic cross-sectional view of a portion of a bulk acoustic wave (BAW) MEMS resonator device 10 useable for fabricating fluidic devices according to embodiments disclosed herein. The resonator device 10 includes a substrate 12 (e.g., typically silicon or another semiconductor material), an acoustic reflector 14 arranged over the substrate 12, a piezoelectric material 22, and bottom and top side electrodes 20, 28. The bottom side electrode 20 is arranged along a portion of a lower surface 24 of the piezoelectric material 22 (between the acoustic reflector 14 and the piezoelectric material 22), and the top side electrode 28 is arranged along a portion of an upper surface 26 of the piezoelectric material 22. An area in which the piezoelectric material 22 is arranged between overlapping portions of the top side electrode 28 and the bottom side electrode 20 is considered an active region 30 of the resonator device 10. The acoustic reflector 14 serves to reflect acoustic waves and therefore reduce or avoid their dissipation in the substrate 12. In certain embodiments, the acoustic reflector 14 includes alternating thin layers 16, 18 of materials (e.g., silicon oxicarbide [SiOC], silicon nitride [$Si_3N_4$], silicon dioxide [$SiO_2$], aluminum nitride [AlN], tungsten [W], and molybdenum [Mo]) having different acoustic impedance values, optionally embodied in a quarter-wave Bragg mirror, deposited over the substrate 12. In certain embodiments, other types of acoustic reflectors may be used. Steps for forming the resonator device 10 may include depositing the acoustic reflector 14 over the substrate 12, followed by deposition of the bottom side electrode 20, followed by growth (e.g., via sputtering or other appropriate methods) of the piezoelectric material 22, followed by deposition of the top side electrode 28.

In certain embodiments, the piezoelectric material 22 comprises a hexagonal crystal structure piezoelectric material (e.g., aluminum nitride or zinc oxide) that includes a c-axis having an orientation distribution that is predominantly non-parallel (and may also be non-perpendicular to) to normal of a face of the substrate 12. Under appropriate conditions, presence of a c-axis having an orientation distribution that is predominantly non-parallel to normal of a face of a substrate enables a BAW resonator to be configured to exhibit a dominant shear response upon application of an alternating current signal across a top side electrode and a bottom side electrode. Methods for forming hexagonal crystal structure piezoelectric materials including a c-axis having an orientation distribution that is predominantly non-parallel to normal of a face of a substrate are disclosed in U.S. patent application Ser. No. 15/293,063 filed on Oct. 13, 2016, with the foregoing application hereby being incorporated by reference herein. Additional methods for forming piezoelectric materials having an inclined c-axis orientation are disclosed in U.S. Pat. No. 4,640,756 issued on Feb. 3, 1987, with the foregoing patent hereby being incorporated by reference herein.

The bulk acoustic wave MEMS resonator device 10 shown in FIG. 1 lacks any layers (e.g., including functionalization material) overlying the active region 30 that would permit the resonator device 10 to be used as a biochemical sensor. If desired, at least portions of the resonator device 10 shown in FIG. 1 (e.g., including the active region 30) may be overlaid with various layers, such as one or more of: a hermeticity layer, an interface layer, a self-assembled monolayer (SAM), and/or functionalization material (which may include specific binding material or non-specific binding material), optionally augmented with blocking material in areas non-coincident with the active region 30.

Figure 2:
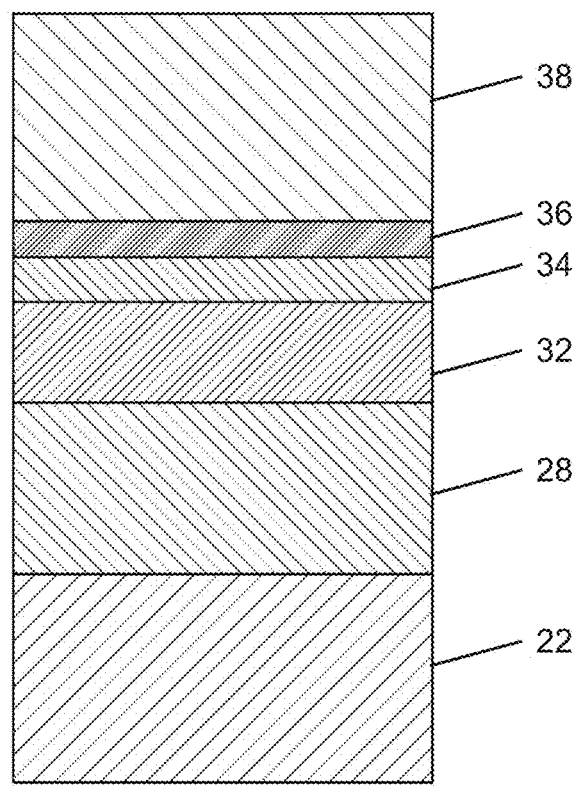
FIG. 2 is a schematic cross-sectional view of an upper portion of a BAW MEMS resonator device including a piezoelectric material and a top side electrode overlaid with a hermeticity layer, an interface layer, a self-assembled monolayer (SAM), and a functionalization (e.g., specific binding) material.

Exemplary Layers Useful with BAW MEMS Resonator Devices for Facilitating Biochemical Sensing Utility FIG. 2 is a schematic cross-sectional view of an upper portion of a BAW MEMS resonator device including a piezoelectric material 22 and a top side electrode 28 overlaid with a hermeticity layer 32, an interface layer 34, a self-assembled monolayer (SAM) 36, and a functionalization (e.g., specific binding) material 38. In certain embodiments, one or more blocking materials (not shown) may be applied during fabrication, such as over portions of an interface layer to prevent localized attachment of one or more subsequently deposited layers, or (if applied over selected regions of a SAM or a functionalization material) to prevent analyte capture in regions not overlying an active region of the BAW MEMS resonator device.

In certain embodiments, photolithography may be used to promote patterning of interface material or blocking material over portions of a MEMS resonator device. Photolithography involves use of light to transfer a geometric pattern from a photomask to a light-sensitive chemical photoresist on a substrate and is a process well known to those of ordinary skill in the semiconductor fabrication art. Typical steps employed in photolithography include wafer cleaning, photoresist application (involving either positive or negative photoresist), mask alignment, and exposure and development. After features are defined in photoresist on a desired surface, an interface layer may be patterned by etching in one or more gaps in a photoresist layer, and the photoresist layer may be subsequently removed (e.g., using a liquid photoresist stripper, by ashing via application of an oxygen-containing plasma, or another removal process).

In certain embodiments, an interface layer (e.g., arrangeable between a top side electrode and a SAM) includes a hydroxylated oxide surface suitable for formation of an organosilane SAM. A preferred interface layer material including a hydroxylated oxide surface is silicon dioxide ($SiO_2$). Alternative materials incorporating hydroxylated oxide surfaces for forming interface layers include titanium dioxide ($TiO_2$), tantalum pentoxide ($Ta_2O_5$), and hafnium oxide ($HfO_2$). Other alternative materials incorporating hydroxylated oxide surfaces will be known to those skilled in the art, and these alternatives are considered to be within the scope of the present disclosure.

In other embodiments, an interface layer (e.g., arrangeable between a top side electrode and a SAM), or at least one electrode that is devoid of an overlying interface layer, includes gold or another noble metal (e.g., ruthenium, rhodium, palladium, osmium, iridium, platinum, or silver) suitable for receiving a thiol-based SAM that may be overlaid with functionalization material.

In certain embodiments incorporating electrode materials subject to corrosion, a hermeticity layer may be applied between a top side electrode and an interface layer. A hermeticity layer may be unnecessary when noble metals (e.g., gold, platinum, etc.) are used for top side electrodes. If provided, a hermeticity layer preferably includes a dielectric material with a low water vapor transmission rate (e.g., no greater than 0.1 g/m²/day). Following deposition of a hermeticity layer and an interface layer, a SAM may be formed over the interface layer, with the SAM including an organosilane material in certain embodiments. The hermeticity layer protects a reactive electrode material (e.g., aluminum or aluminum alloy) from attack in corrosive liquid environments, and the interface layer facilitates proper chemical binding of the SAM.

In certain embodiments, a hermeticity layer and/or an interface layer may be applied via one or more deposition processes such as atomic layer deposition (ALD), chemical vapor deposition (CVD), or physical vapor deposition (PVD). Of the foregoing processes, ALD is preferred for deposition of at least the hermeticity layer (and may also be preferable for deposition of the interface layer) due to its ability to provide excellent conformal coating with good step coverage over device features so as to provide layer structures that are free of pinholes. Moreover, ALD is capable of forming uniformly thin layers that provide relatively little damping of acoustic vibrations that would otherwise result in degraded device performance. Adequacy of coverage is important for a hermeticity layer (if present) to avoid corrosion of the underlying electrode. If ALD is used for deposition of a hermeticity layer, then in certain embodiments, a hermeticity layer may include a thickness in a range of from about 10 nm to about 25 nm. In certain embodiments, hermeticity layer thickness is about 15 nm, or from about 12 nm to about 18 nm. Conversely, if another process such as chemical vapor deposition is used, then a hermeticity layer may include a thickness in a range of from about 80 nm to about 150 nm or more, or in a range of from about 80 nm to about 120 nm. Considering both of the foregoing processes, hermeticity layer thicknesses may range from about 5 nm to about 150 nm. If ALD is used for deposition of an interface layer, then an interface layer may include a thickness in a range of from about 5 nm to about 15 nm. In certain embodiments, an interface layer may include a thickness of about 10 nm, or in a range of from about 8 nm to about 12 nm. Other interface layer thickness ranges and/or deposition techniques other than ALD may be used in certain embodiments. In certain embodiments, a hermeticity layer and an interface layer may be sequentially applied in a vacuum environment, thereby promoting a high-quality interface between the two layers.

If provided, a hermeticity layer may include an oxide, a nitride, or an oxynitride material serving as a dielectric material and having a low water vapor transmission rate (e.g., no greater than 0.1 g/m²/day) according to certain embodiments. In certain embodiments, a hermeticity layer includes at least one of aluminum oxide ($Al_2O_3$) or silicon nitride (SiN). In certain embodiments, an interface layer includes at least one of $SiO_2$, $TiO_2$, or $Ta_2O_5$. In certain embodiments, multiple materials may be combined in a single hermeticity layer, and/or a hermeticity layer may include multiple sublayers of different materials. Preferably, a hermeticity layer is further selected to promote compatibility with an underlying reactive metal (e.g., aluminum or aluminum alloy) electrode structure of a BAW resonator. Although aluminum or aluminum alloys are frequently used as electrode materials in BAW resonators, various transition and post-transition metals can be used for such electrodes.

Following deposition of an interface layer (optionally arranged over an underlying hermeticity layer), a SAM is preferably formed over the interface layer. SAMs are typically formed by exposure of a solid surface to amphiphilic molecules with chemical groups that exhibit strong affinities for the solid surface. When an interface layer comprising a hydroxylated oxide surface is used, then organosilane SAMs are particularly preferred for attachment to the hydroxylated oxide surface. Organosilane SAMs promote surface bonding through silicon-oxygen (Si—O) bonds. More specifically, organosilane molecules include a hydrolytically sensitive group and an organic group and are therefore useful for coupling inorganic materials to organic polymers. An organosilane SAM may be formed by exposing a hydroxylated oxide surface to an organosilane material in the presence of trace amounts of water to form intermediate silanol groups. These groups then react with free hydroxyl groups on the hydroxylated oxide surface to covalently immobilize the organosilane. Examples of possible organosilane-based SAMs that are compatible with interface layers incorporating hydroxylated oxide surfaces include 3-glycidoxypropyltrimethoxysilane (GPTMS), 3-mercaptopropyltrimethoxysilane (MPTMS), 3-aminopropyltrimethoxysilane (APTMS), and octadecyltrimethoxysilane (OTMS), including their ethoxy- and chloro-variants. Additional silanes that may be used for SAMs include poly(ethylene glycol) (PEG) conjugated variants. Those skilled in the art will recognize that other alternatives exist, and these alternatives are considered to be within the scope of the present disclosure. An exemplary SAM may include a thickness in a range of at least 0.5 nm or more. Preferably, a SAM readily binds to the locally patterned interface layer but does not readily bind to other adjacent material layers (e.g., a hermeticity layer, a piezoelectric material, and/or a blocking material layer).

When an electrode and/or interface layer comprising gold or another noble metal is used, then thiol-based (e.g., alkanethiol-based) SAMs may be used. Alkanethiols are molecules with an S—H head group, a tail group, and a back bone comprising an alkyl chain. Thiols may be used on noble metal interface layers due to the strong affinity of sulfur for these metals. Examples of thiol-based SAMs that may be used include, but are not limited to, 1-dodecanethiol (DDT), 11-mercaptoundecanoic acid (MUA), and hydroxyl-terminated (hexaethylene glycol) undecanethiol (1-UDT). These thiols contain the same backbone, but different end groups—namely, methyl ($CH_3$), carboxyl (COOH), and hydroxyl-terminated hexaethylene glycol (HO—$(CH_2CH_2O)_6$) for DDT, MUA, and 1-UDT, respectively. In certain embodiments, SAMs may be formed by incubating gold surfaces in thiol solutions using a suitable solvent, such as anhydrous ethanol.

Following formation of a SAM, the SAM may be biologically functionalized, such as by receiving at least one functionalization (e.g., specific binding) material. In certain embodiments, functionalization materials may be applied on or over a SAM using a microarray spotting needle or other suitable methods. In certain embodiments, an interface layer may be patterned (e.g., using photolithography and selective etching for defining the interface layer) with a high dimensional tolerance over only a portion of a BAW resonator (which includes a substrate), a SAM may be applied over the interface layer, and a subsequently applied functionalization material may be attached only to the SAM. In certain embodiments, patterning of an interface layer may provide a higher dimensional tolerance for positioning of the functionalization material than could be attained by microarray spotting alone. Examples of specific binding materials include, but are not limited to, antibodies, receptors, ligands, and the like. A specific binding material is preferably configured to receive a predefined target species (e.g., molecule, protein, DNA, virus, bacteria, etc.). A functionalization material including specific binding material may include a thickness in a range of from about 5 nm to about 1000 nm, or from about 5 nm to about 500 nm. In certain embodiments, an array of different functionalization (e.g., specific binding) materials may be provided over different active regions of a multi-resonator structure (i.e., one or more resonator structures including multiple active regions), optionally in combination with one or more active regions that are devoid of functionalization materials to serve as comparison (or "reference") regions. In certain embodiments, a functionalization material (e.g., bio-functionalization) may provide non-specific binding utility.

Exemplary Fluidic Devices Incorporating BAW MEMS Resonator Devices

Fluidic devices may include one or more bulk acoustic wave MEMS resonator devices as disclosed herein and at least one fluidic passage (e.g., a channel, a chamber, or the like) arranged to conduct a liquid to contact at least one functionalization (e.g., specific binding) material arranged over at least one active region. Such a device may be microfluidic in scale, and may comprise at least one microfluidic passage (e.g., having at least one dimension, such as height and/or width, of no greater than about 500 microns, or about 250 microns, or about 100 microns). For example, following fabrication of bulk acoustic wave MEMS resonator devices and deposition of a SAM over portions thereof (optionally preceded by deposition of a hermeticity layer and an interface layer), a microfluidic device may be fabricated by forming one or more walls defining lateral boundaries of a microfluidic channel over a first bulk acoustic wave MEMS resonator device with an active region thereof arranged along a bottom surface of the microfluidic channel, and then enclosing the microfluidic passage using a cover or cap layer that may define fluidic ports (e.g., openings) enabling fluid communication with the microfluidic channel. In certain embodiments, functionalization (e.g., specific binding) material may be pre-applied to an active region of a bulk acoustic wave MEMS resonator device before formation of a microfluidic channel; in other embodiments, functionalization material may be applied over an active region of a bulk acoustic wave resonator following formation of a microfluidic channel.

Walls of a microfluidic channel may be formed of any suitable material, such as laser-cut "stencil" layers of thin polymeric materials and/or laminates, optionally including one or more self-adhesive surfaces (e.g., adhesive tape). Optionally such walls may be formed prior to deposition of a SAM layer, functionalization material, and/or blocking layers, with an SU-8 negative epoxy resist or other photoresist material. In certain embodiments, a cover or cap layer may be integrally formed with one or more walls (e.g., via molding or another suitable process) to define a portion of an upper boundary as well as lateral boundaries of at least one microfluidic channel, and the integrally formed partial cover/wall structure may be applied (e.g., adhered or otherwise bonded) over at least a portion of a bulk acoustic wave resonator to enclose the at least one microfluidic channel.

In certain embodiments, a chemical or biological blocking material may be applied over a portion of a SAM to prevent attachment of a functionalization (e.g., specific binding) material over one or more selected regions of a BAW resonator (e.g., one or more regions apart from an active region). The proper choice of a chemical or biological blocking material (e.g., blocking buffer) for a given analysis depends on the type of target species or analyte present in a sample. Various types of blocking buffers such as highly purified proteins, serum, or milk may be used to block free sites on a SAM. Additional blockers include ethanolamine or polyethylene oxide (PEO)-containing materials. An ideal blocking buffer would bind to all potential sites of non-specific interaction away from an active region. To optimize a blocking buffer for a particular analysis, empirical testing may be used to determine signal-to-noise ratio. No single chemical or biological blocking material is ideal for every situation, since each antibody-antigen pair has unique characteristics.

Figure 3:
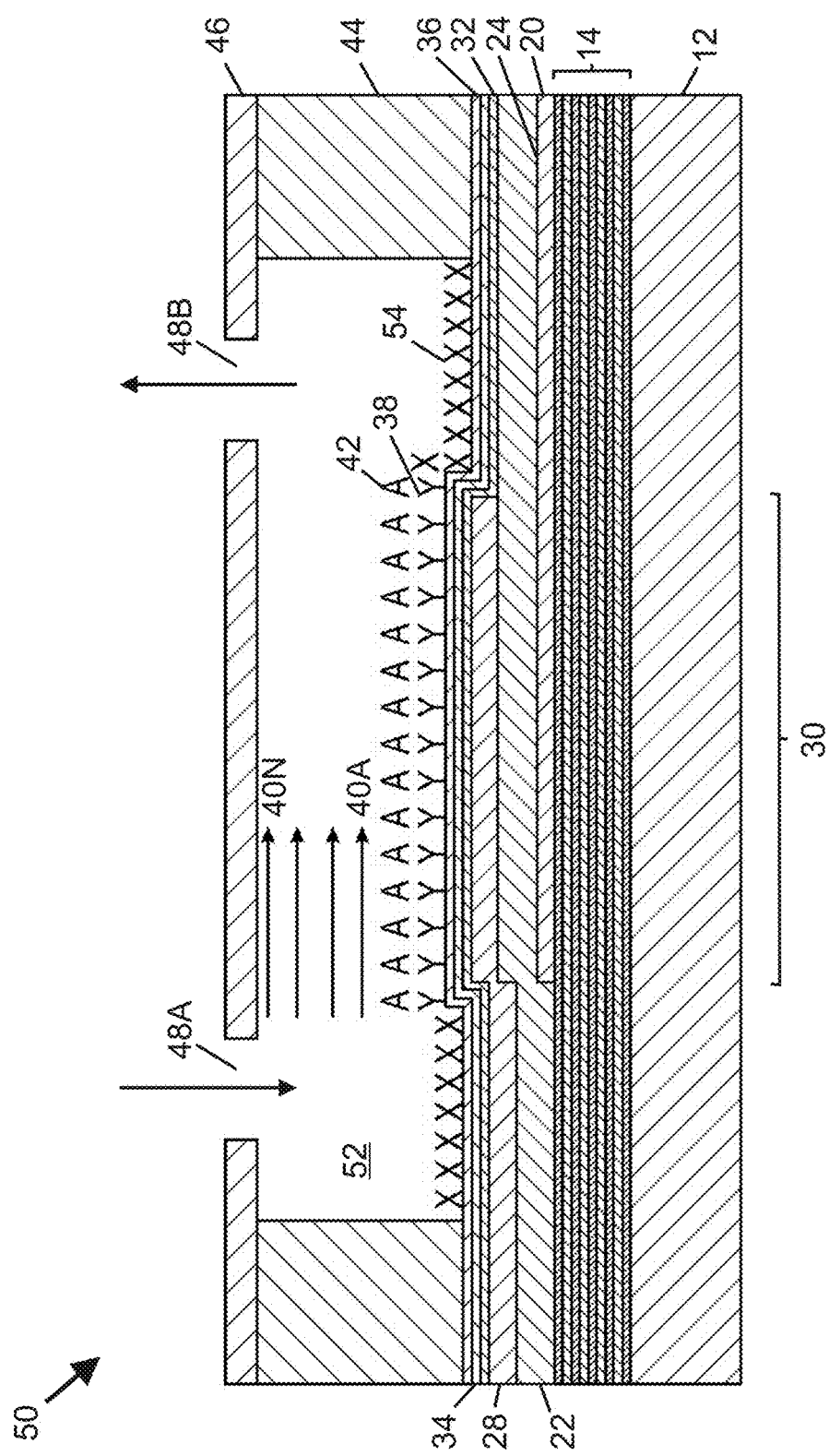
FIG. 3 is a schematic cross-sectional view of a portion of a fluidic device (e.g., a biochemical sensor device) including a fluidic passage bounded from below by a BAW resonator, bounded laterally by walls, and bounded from above by a cover or cap layer, with an interface layer and a self-assembled monolayer (SAM) arranged over the entirety of a piezoelectric material, and with a blocking material arranged over portions of the SAM non-coincident with an active region distal from fluidic ports defined in the cover or cap layer, with the fluidic device being useable (optionally in combination with an instrument and/or system) for performing steps of temperature compensation and/or operational configuration methods as disclosed herein, according to one embodiment.

FIG. 3 is a schematic cross-sectional view of a portion of a fluidic device 50 (e.g., a biochemical sensor device) including a fluidic passage 52 that is bounded from below by a bulk acoustic wave (BAW) MEMS resonator device including an active region 30, bounded laterally by walls 44, and bounded from above by a cover or cap layer 46 defining fluidic ports 48A, 48B, with the fluidic device 50 being useable with various embodiments disclosed herein. The fluidic device 50 includes a substrate 12 overlaid with an acoustic reflector 14, and a bottom side electrode 20 arranged generally below a piezoelectric material 22 (i.e., along a lower surface 24 of the piezoelectric material 22). A top side electrode 28 extends over a portion of the piezoelectric material 22, wherein a portion of the piezoelectric material 22 arranged between the top side electrode 28 and the bottom side electrode 20 embodies the active region 30 of the BAW MEMS resonator device. The top side electrode 28 and the piezoelectric material 22 are overlaid with a hermeticity layer 32, an interface layer 34, and a self-assembled monolayer (SAM) 36. Portions of the SAM 36 between the active region 30 and the walls 44 are overlaid with a chemical or biological blocking material 54 to prevent localized attachment of functionalization material and/or analyte. A portion of the SAM 36 that is registered with the active region 30 is overlaid with a layer of functionalization (e.g., specific binding) material 38 arranged to bind at least one analyte (e.g., analyte 42). Walls 44 that are laterally displaced from the active region 30 extend upward from the SAM 36 to define lateral boundaries of the fluidic passage 52 containing the active region 30. The walls 44 may be formed of any suitable material, such as a laser-cut "stencil" layer of thin polymeric materials and/or laminate materials, optionally including one or more self-adhesive surfaces (e.g. adhesive tape). Optionally such walls 44 may be formed prior to deposition of the SAM 36, functionalization material 38, and chemical or biological blocking material 54 with an SU-8 negative epoxy resist or other photoresist material. The cover or cap layer 46 defining upper surface fluidic ports 48A, 48B is further provided to provide an upper boundary for the fluidic passage 52. The cover or cap layer 46 may be formed by defining ports (e.g., via laser cutting or water jet cutting) in a layer of an appropriate material (e.g., a substantially inert polymer, glass, silicon, ceramic, or the like), and adhering the cover or cap layer 46 to top surfaces of the walls 44.

In use of the fluidic device 50, a fluid sample may be supplied through the first fluidic port 48A into the fluidic passage 52 over the active region 30 and through the second fluidic port 48B to exit the fluidic passage 52. Due to the laminar nature of the fluid flow within the fluidic passage 52, the fluid volume may be modeled and behave as a "stack" of horizontal fluid layers including a lowermost fluid layer 40A and an uppermost fluid layer 40N. A suitable analyte 42 contained in the lowermost fluid layer(s) (e.g., layer 40A) of the fluid sample will tend to bind with functionalization material 38 arranged over the active region 30. Analyte contained in fluid layers above the lowermost fluid layer 40A (including the uppermost fluid layer 40N) may be less available to bind with the functionalization material 38. When a bulk acoustic wave having a dominant shear component is induced in the active region 30 by supplying an electrical (e.g., alternating current) signal of a desired frequency to the bottom and top side electrodes 20, 28, a change in electroacoustic response (e.g., at least one of an amplitude-magnitude property, a frequency property, or a phase property, such as a shift in resonant frequency) of the BAW resonator may be detected to indicate a presence and/or quantity of analyte 42 bound to the functionalization material 38.

Figure 4:
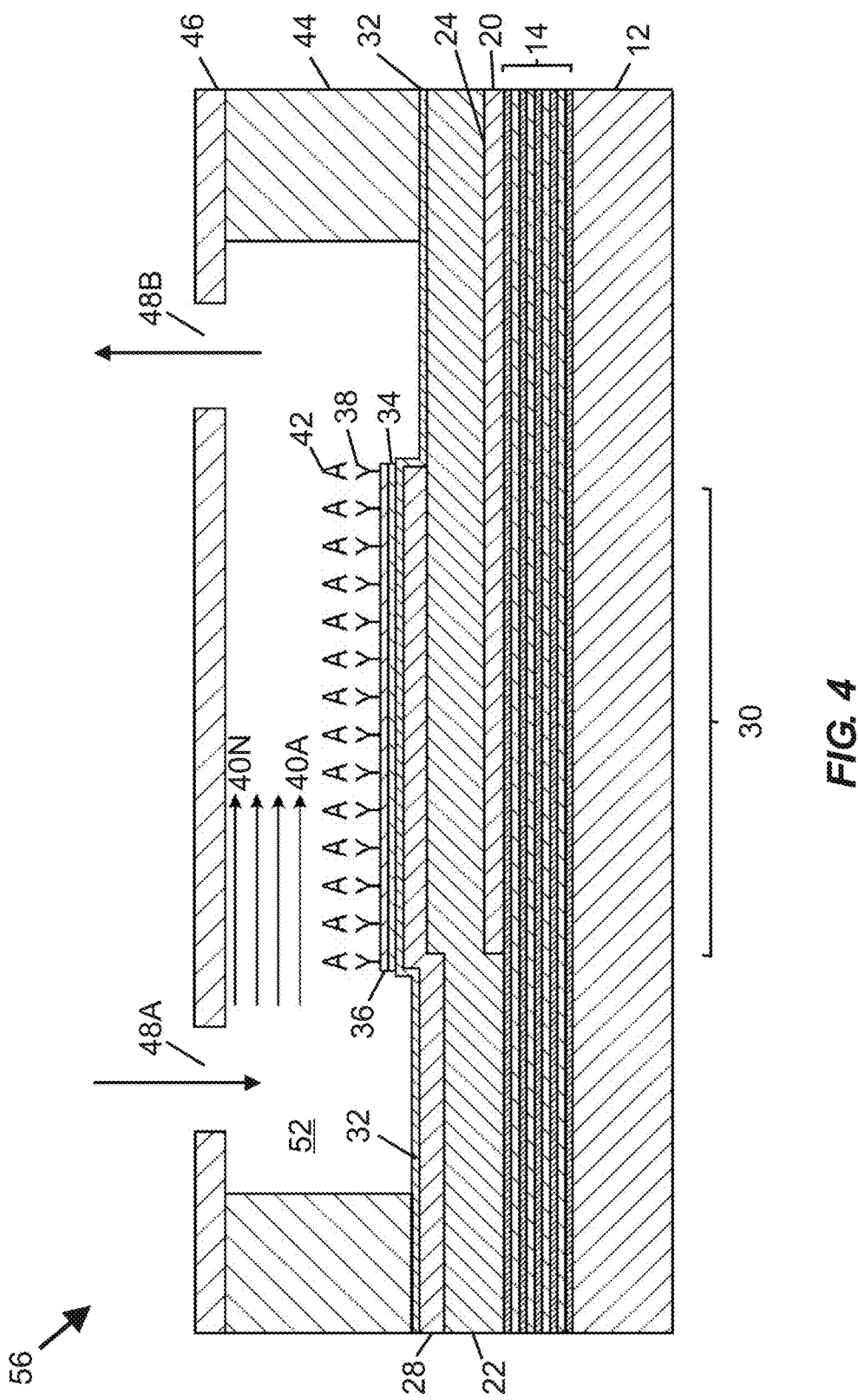
FIG. 4 is a schematic cross-sectional view of a portion of a fluidic device (e.g., a biochemical sensor device) similar to the fluidic device of FIG. 3, but including an interface layer, a SAM, and functionalization material arranged only over an active region distal from fluidic ports defined in the cover or cap layer.

FIG. 4 is a schematic cross-sectional view of a portion of a fluidic device (e.g., a biochemical sensor device) 56 similar to the fluidic device 50 of FIG. 3, but including an interface layer 34 and a SAM 36 that are provided solely over an active region 30 instead of over an entirety of piezoelectric material 22. Such configuration may be provided by patterning of the interface layer 34. The fluidic device 56 includes a fluidic passage 52 that is bounded from below by a bulk acoustic wave MEMS resonator device including the active region 30, bounded laterally by walls 44, and bounded from above by a cover or cap layer 46 defining fluidic ports 48A, 48B. The fluidic device 56 includes a substrate 12 overlaid with an acoustic reflector 14, and a bottom side electrode 20 arranged generally below the piezoelectric material 22 (i.e., along a lower surface 24 of the piezoelectric material 22). A top side electrode 28 extends over a portion of the piezoelectric material 22, wherein a portion of the piezoelectric material 22 arranged between the top side electrode 28 and the bottom side electrode 20 embodies the active region 30 of the BAW MEMS resonator device. A hermeticity layer 32 is arranged over the top electrode 28 and the piezoelectric material 22. The interface layer 34 and the SAM 36 are provided over a portion of the hermeticity layer 32 registered with the active region 30. The SAM 36 is overlaid with a layer of functionalization (e.g., specific binding) material 38 arranged to bind at least one analyte (e.g., analyte 42). Walls 44 that are laterally displaced from the active region 30 extend upward from the hermeticity layer 32 to define lateral boundaries of the fluidic passage 52 containing the active region 30. The cover or cap layer 46 defining upper surface fluidic ports 48A, 48B is provided over the walls 44 to provide an upper boundary for the microfluidic passage 52. Operation of the fluidic device 56 of FIG. 4 is similar to the operation of the fluidic device 50 of FIG. 3. A volume of fluid may behave as a "stack" of horizontal fluid layers including a lowermost fluid layer 40A and an uppermost fluid layer 40N within the fluidic passage 52, wherein the lowermost fluid layer 40A is proximate to functionalization material 38 overlying the active region 30.

Although FIGS. 1, 3, and 4 are directed to solidly mounted BAW resonators employing acoustic reflectors between substrates and electrodes, it is to be appreciated that methods disclosed herein are equally applicable to film bulk acoustic wave resonator (FBAR) structures, such as disclosed in FIGS. 5A and 5B.

FIG. 5A is a schematic cross-sectional view of a film bulk acoustic wave resonator (FBAR) structure 60 including an active region 30, wherein at least portions of the active region 30 are subject to being overlaid with an interface layer and a self-assembled monolayer (SAM) suitable for receiving a functionalization (e.g., specific binding or non-specific binding) material, according to one embodiment. The FBAR structure 60 includes a substrate 62 (e.g., silicon or another semiconductor material) defining a cavity 64 optionally covered by a support layer 66 (e.g., silicon dioxide). A bottom side electrode 20 is arranged over a portion of the support layer 66, a piezoelectric material 22, preferably embodying inclined c-axis hexagonal crystal structure piezoelectric material (e.g., AlN or ZnO), is arranged over the bottom side electrode 20 and the support layer 66, and a top side electrode 28 is arranged over at least a portion of a top surface of the piezoelectric material 22. A portion of the piezoelectric material 22 arranged between the top side electrode 28 and the bottom side electrode 20 embodies the active region 30 of the FBAR structure 60. The active region 30 is arranged over and registered with the cavity 64 disposed below the support layer 66. The cavity 64 serves to confine acoustic waves induced in the active region 30 by preventing dissipation of acoustic energy into the substrate 62, since acoustic waves do not efficiently propagate across the cavity 64. In this respect, the cavity 64 provides an alternative to the acoustic reflector 14 illustrated in FIGS. 1, 3, and 4. Although the cavity 64 shown in FIG. 5A is bounded from below by a thinned portion of the substrate 62, in alternative embodiments at least a portion of the cavity 64 may extend through an entire thickness of the substrate 62. Steps for forming the FBAR structure 60 may include defining the cavity 64 in the substrate 62, filling the cavity 64 with a sacrificial material (not shown) optionally followed by planarization of the sacrificial material, depositing the support layer 66 over the substrate 62 and the sacrificial material, removing the sacrificial material (e.g., by flowing an etchant through vertical openings defined in the substrate 62 or the support layer 66, or lateral edges of the substrate 62), depositing the bottom side electrode 20 over the support layer 66, growing (e.g., via sputtering or other appropriate methods) the piezoelectric material 22, and depositing the top side electrode 28. In certain embodiments, the top side electrode 28, the piezoelectric material 22, and the bottom side electrode 20 in combination may be self-supporting, and the support layer 66 may be omitted and/or removed by etching in the vicinity of the active region 30.

FIG. 5B is a schematic cross-sectional view of the FBAR structure 60 according to FIG. 5A, following addition of a hermeticity layer 32, an interface layer 34, a self-assembled monolayer (SAM) 36, and functionalization material 38 (e.g., specific binding material). The hermeticity layer 32 is arranged over the entire piezoelectric material 22 (as well as the top side electrode 28), whereas the functionalization material 38, the SAM 36, and the interface layer 34 are arranged solely over the active region 30. As shown in FIG. 5B, analyte 42 is bound to the functionalization material 38, such as may occur following exposure of the functionalization material 38 to a medium (e.g., liquid or other fluid) containing the analyte 42, optionally as part of a microfluidic device.

Figure 6:
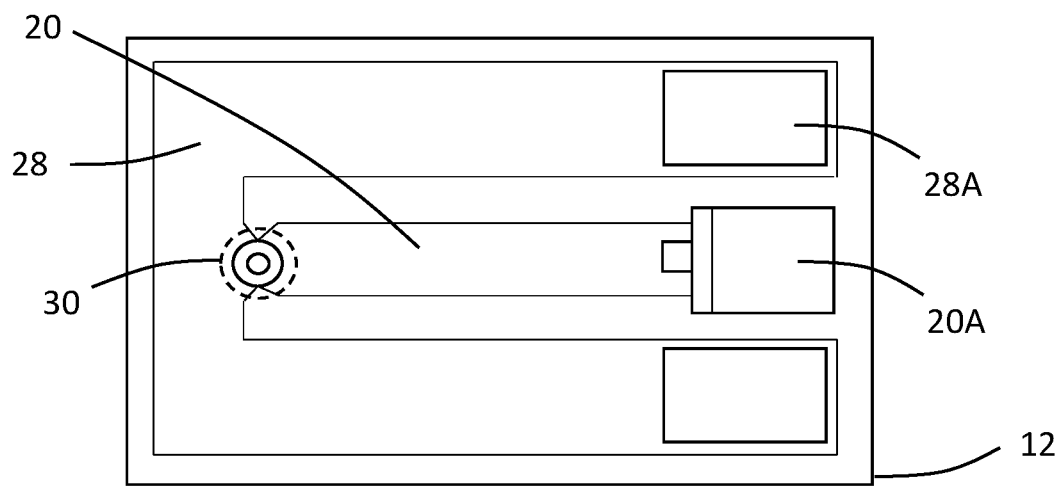
FIG. 6 is a schematic top plan view of a BAW MEMS resonator device suitable for receiving a hermeticity layer, an interface layer, a self-assembled monolayer, and functionalization (e.g. specific binding) material as disclosed herein.

FIG. 6 is a top plan view photograph of a bulk acoustic wave MEMS resonator device 10 (consistent with the portion of the resonator device 10 illustrated in FIG. 1) suitable for receiving a hermeticity layer, an interface layer, a self-assembled monolayer, and/or functionalization (e.g., specific binding) material as disclosed herein. The MEMS resonator device 10 includes a piezoelectric material (not shown) arranged over a substrate 12, a bottom side electrode 20 arranged under a portion of the piezoelectric material, and a top side electrode 28 arranged over a portion of the piezoelectric material, including an active region 30 in which the piezoelectric material is arranged between overlapping portions of the top side electrode 28 and the bottom side electrode 20. Externally accessible contacts 20A, 28A are in electrical communication with the bottom side electrode 20 and the top side electrode 28, respectively. After portions of the resonator device 10 are overlaid with a hermeticity layer, an interface layer, a self-assembled monolayer, and functionalization (e.g., specific binding) material as disclosed herein, the resonator device 10 may be used as a sensor and/or incorporated into a microfluidic device. If desired, multiple resonator devices 10 may be provided in an array on a single substrate 12.

Figure 7:
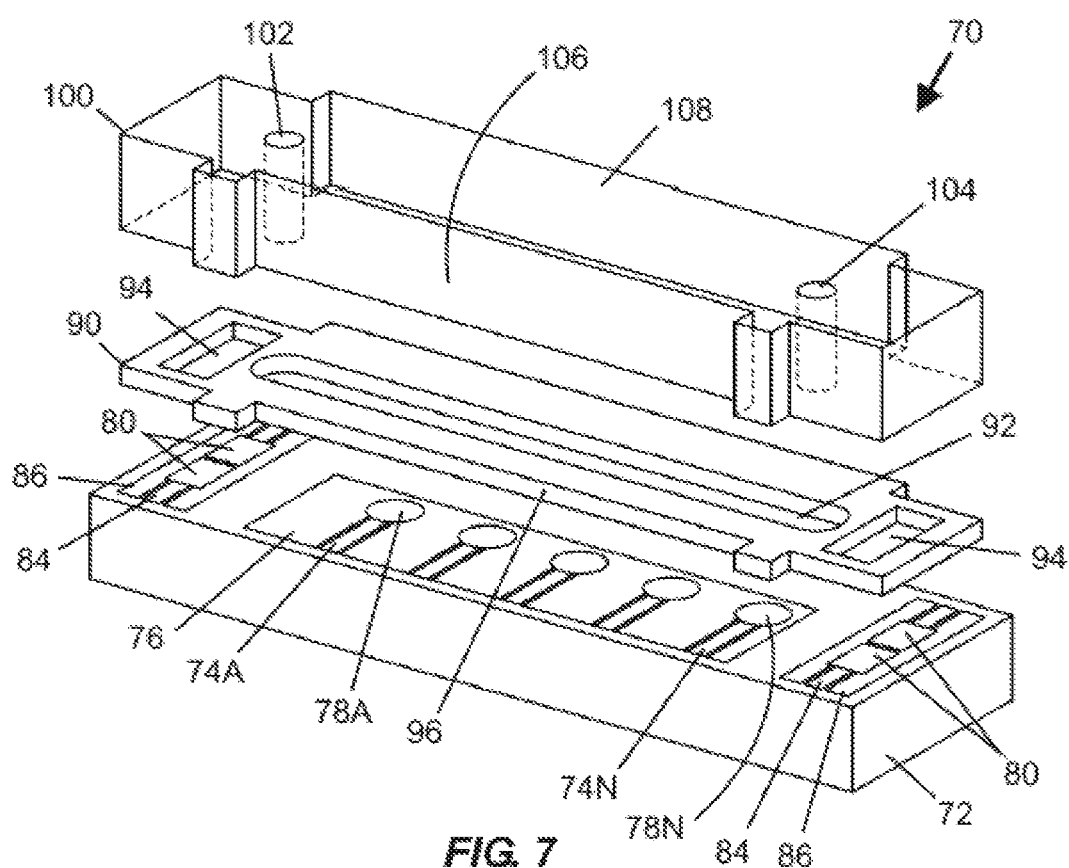
FIG. 7 is a perspective assembly view of a microfluidic device incorporating a substrate including multiple bulk BAW MEMS resonator devices as disclosed herein, an intermediate wall structure layer defining lateral boundaries of a central microfluidic channel registered with active regions of the MEMS resonator devices, and a cover or cap layer defining an upper boundary of the central microfluidic channel.

FIG. 7 is a perspective assembly view of a microfluidic device 70 incorporating a substrate 72 including multiple bulk acoustic wave MEMS resonator devices, an intermediate (e.g., wall defining) layer 90 defining lateral boundaries of a central microfluidic channel 92 registered with active regions 78A-78N of the MEMS resonator devices, and a cover or cap layer 100 arranged to cover the intermediate layer 90 and defining an upper boundary of the central microfluidic channel 92. Top central portions of the substrate 72 (which preferably includes an acoustic reflector (not shown) and a piezoelectric material (not shown)), include a top side electrode 76 and bottom side electrodes 74A-74N. Regions in which the foregoing electrodes overlap one another and sandwich the piezoelectric material embody active regions 78A-78N. Any suitable number of active regions 78A-78N may be provided and fluidically arranged in series or parallel, although five active regions are illustrated in FIG. 7. Top peripheral (or top end) portions of the substrate 72 further include reference top side electrodes 86 and reference bottom side electrodes 84 in communication with reference overlap regions 80. Such reference overlap regions 80 are not exposed to fluid, and are present to provide a basis for comparing signals obtained from the active regions 78A-78N exposed to fluid within the central microfluidic channel 92. The substrate 72 is overlaid with the intermediate (e.g., wall-defining) layer 90, wherein the central microfluidic channel 92 is intended to receive fluid, and defines peripheral chambers 94 arranged to overlie the reference overlap regions 80 in a sealed fashion. The intermediate layer 90 may be formed of any suitable material such as SU-8 negative epoxy resist, other photoresist material, or laser-cut "stencil" layers of thin polymeric materials optionally including one or more self-adhesive surfaces (e.g., adhesive tape), etc. A lateral inset region 96 of the intermediate layer 90 enables access to lateral portions of the top side electrode 76 and bottom side electrodes 74A-74N. The cover or cap layer 100 includes a lateral inset region 106 registered with the lateral inset region 96 of the intermediate layer 90, and includes microfluidic ports 102, 104 accessible along a top surface 108 and registered with end portions of the central microfluidic channel 92 in the intermediate layer 90 to permit fluid (e.g., liquid) to be supplied to the central microfluidic channel 92 over the active regions 78A-78N. Preferably, at least the electrodes 74A-74N, 76 are overlaid with a hermeticity layer, an interface layer, a self-assembled monolayer, and functionalization (e.g., specific binding) material as disclosed herein. Fluidic (e.g., microfluidic) devices according to other configurations may be provided, as will be recognized by those skilled in the art upon review of the present disclosure.

Exemplary Electrical Components of a Sensing System

Figure 8A:
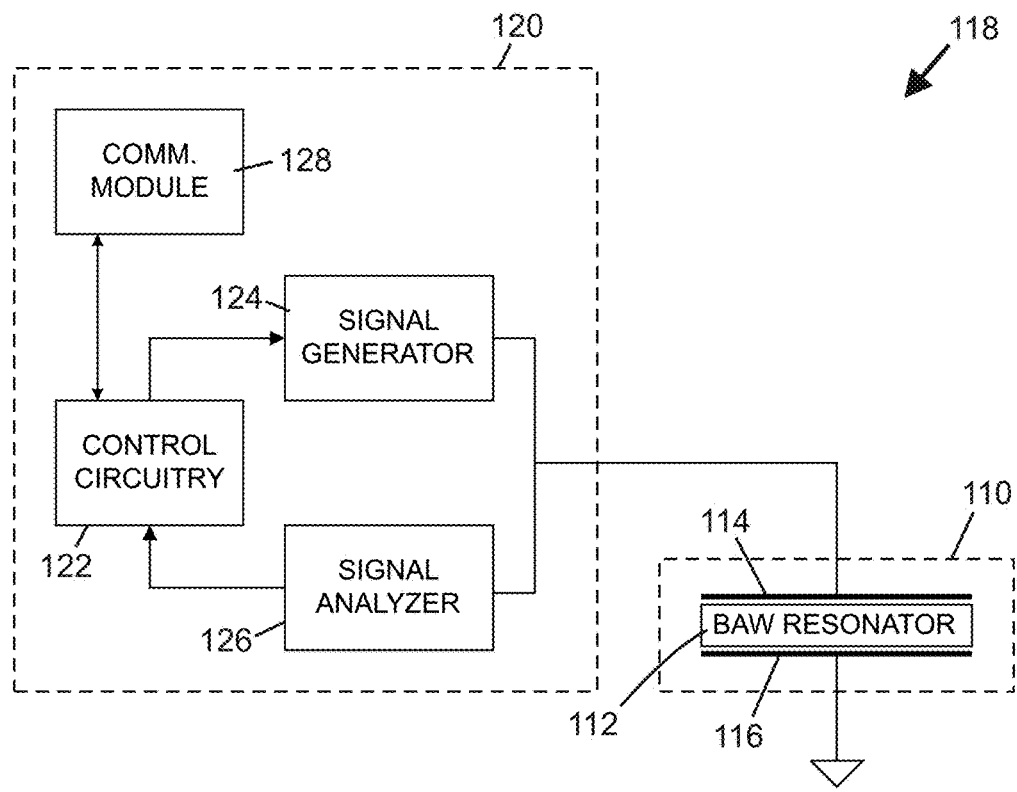
FIG. 8A is a schematic block diagram showing electrical components of a sensing system including a BAW resonator according to one embodiment.

FIG. 8A is a schematic block diagram showing electrical components of a sensing system 118 including a BAW resonator 112 according to one embodiment. The sensing system 118 includes a sensing portion 110 and a control portion 120. In certain embodiments, the sensing portion 110 may be embodied in a fluidic device configured as a cartridge that is suitable for use with an instrument that includes the control portion 120. In other embodiments, one or more components of the control portion 120 may be integrated with a fluidic device that includes the sensing portion 110. Within the sensing portion 110, the BAW resonator 112 includes top side and bottom side electrodes 114, 116, with at least one electrode 114, 116 being arranged in electrical communication with the control portion 120. The control portion 120 includes control circuitry 122 arranged to provide signals to a signal generator 124, and arranged to receive signals from a signal analyzer 126. The control circuitry 122 may also be coupled with a communication module 128.

The control circuitry 122 may include a central processing unit (CPU) and memory to enable the control circuitry 122 to directionally or bi-directionally communicate with the communication module 128 or other devices over a communication bus or another appropriate communication interface. The control circuitry 122 may communicate output information and/or receive instructions from the communication module 128. In certain embodiments, the signal analyzer 126 may include a digital signal processing module.

In certain embodiments, the control circuitry 122 may be used to control operation of the signal generator 124 to adjust at least one alternating current signal supplied to the BAW resonator 112. In certain embodiments, an alternating current signal configured to cause the BAW resonator 112 to exhibit a dominant shear response may be controlled to provide a sweep of adjacent frequencies in order to enable detection a resonant frequency of the BAW resonator 112. Such resonant frequency may be altered based on adsorption of mass (e.g., analyte) to functionalization material associated with the BAW resonator 112. In this manner, performance of frequency sweeps prior to and after exposure of the BAW resonator 112 (including an active region overlaid with functionalization material) to analyte may be used to detect changes in resonant frequency indicative of presence and/or concentration of analyte bound to (e.g., adsorbed by) the functionalization material. The control portion 120 may further utilize a hill-climbing algorithm to locate a maximum amplitude at the resonant frequency of the BAW resonator 112.

With continued reference to FIG. 8A, the signal generator 124 preferably includes one or more oscillators arranged to output alternating current signals of different frequencies. In certain embodiments, the signal generator 124 may include a voltage controlled oscillator with a frequency dependent on an input voltage bias, providing an alternating current (e.g., square wave) output waveform with an output frequency that may be tuned with appropriate biasing resistors and capacitors.

In certain embodiments, the signal analyzer 126 is configured to receive one or more signals indicative of electroacoustic response of the BAW resonator 112 (such as voltage, current, frequency, and/or phase, to name a few). These signals may be received by the signal analyzer 126 while the BAW resonator 112 receives a signal from the signal generator 124 configured to cause the BAW resonator 112 to exhibit a dominant shear response.

Figure 8B:
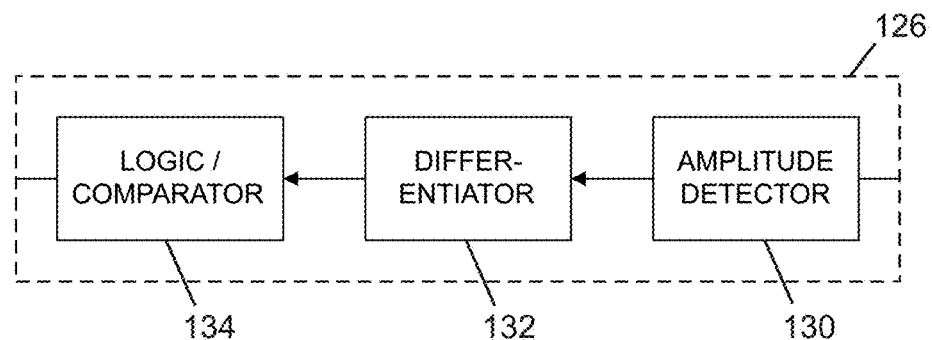
FIG. 8B is a schematic block diagram showing stages internal to a signal analyzer of the electrical components of the sensing system depicted in FIG. 8A.

FIG. 8B is a schematic block diagram showing stages internal to the signal analyzer 126 of the electrical components of the sensing system 118 depicted in FIG. 8A. In certain embodiments, the signal analyzer 126 may include an amplitude detector stage 130, a differentiator stage 132, and a logic (or comparator) stage 134. An exemplary amplitude detector stage 130 may include a high-pass filter, an amplifier, a precision full-wave rectifier, and a low-pass filter arranged in sequence. A high-pass filtered input signal received from the BAW resonator 112 may be amplified and then rectified, whereby the amplitude may be obtained by capturing the envelope of the rectified signal using the low-pass filter. The differentiator stage 132 may be composed of low-pass filters and a differentiator to determine the change in resonator signal with respect to time. The logic (or comparator) stage 134 may determine the direction of sweep based on a change in response with respect to time, and may trigger a change in direction in a hill-climbing function when a differentiation signal changes from positive to negative. An exemplary logic (or comparator) stage 134 may include a comparator, a toggle flip flop, and an integrator. The integrator of the logic (or comparator) stage 134 may be used to integrate the digital signal of the comparator and generate an output signal of the signal analyzer 126 that may be provided to the control circuitry 122. Such signal may optionally be communicated by the control circuitry 122 to the signal generator 124 and/or the communication module 128 (shown in FIG. 8A). Although FIG. 8A discloses circuitry suitable for driving the BAW resonator 112, and FIGS. 8A and 8B disclose circuitry suitable for detecting a change in electroacoustic response of the BAW resonator 112, it is to be appreciated that other driving circuits and/or detection circuits may be used.

Exemplary Liquid Supply Switching Sensor Test Apparatus

Figures 9, 12B:
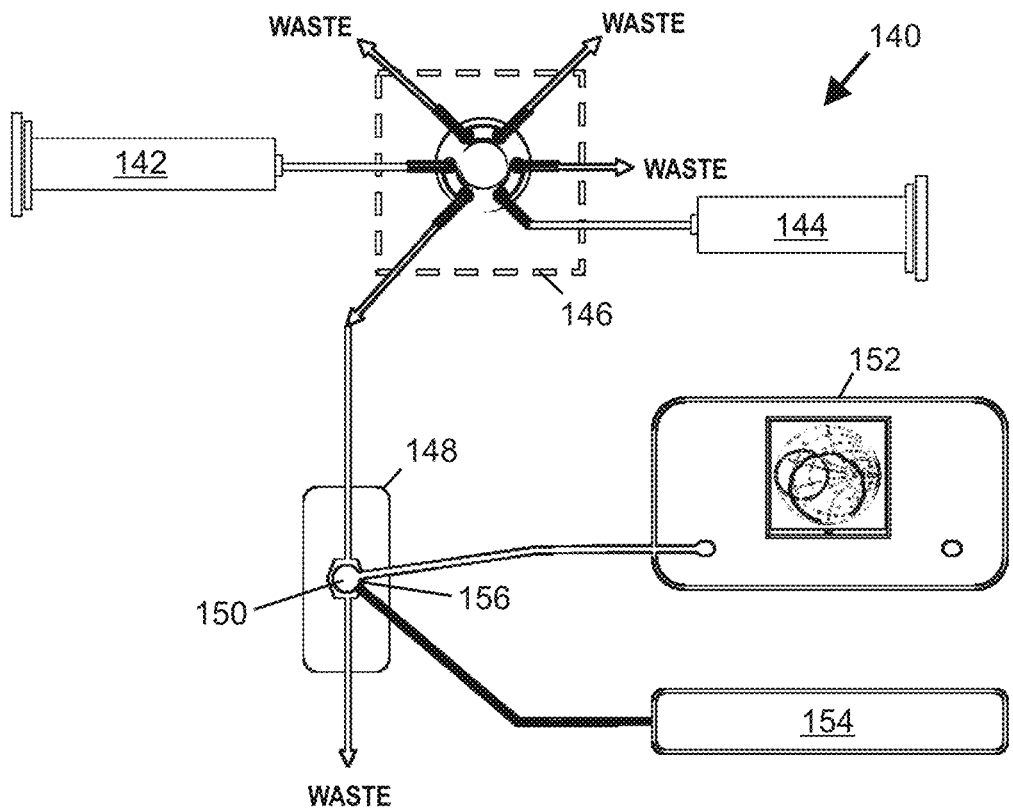
FIG. 9 is a schematic diagram showing interconnections between components of a liquid supply switching sensor test apparatus used to perform experiments and generate data supporting the present disclosure.
FIG. 12B is a table identifying frequency shift (kHz) and sensitivity (kHz/% glycerine) as a function of phase crossing where the frequency shift is monitored, corresponding to the plots shown in FIG. 12A.

FIG. 9 is a schematic diagram illustrating interconnections between components of a liquid supply switching sensor test apparatus 140 used to perform experiments and generate data supporting the present disclosure. The test apparatus 140 includes first and second syringe pumps 142, 144 arranged to supply a first liquid (glycerine/deionized (DI) water mixture) and a second liquid (DI water), respectively, to a dual position switching valve 146 arranged to convey liquid of a microfluidic chamber 148 incorporating a BAW resonator sensing device 150. A change of state of the dual position switching valve 146 is configured to change the supply of liquid to the microfluidic chamber 148 from deionized (DI) water to the glycerine/DI water mixture, or vice-versa. A vector network analyzer 152 coupled to the BAW resonator sensing device 150 is configured to sweep the portion of the resonant loop closest to the origin on a Smith chart—representing a location where phase is changing rapidly. Because of liquid loading of the BAW resonator sensing device 150, the phase is described by negative phase angles (i.e., the BAW resonator sensing device 150 was not inductive during these measurements). Temperature of the BAW resonator sensing device 150 was monitored by placement of two K-type thermocouples 156 in intimate contact with a substrate of the BAW resonator sensing device 150. Signals from the two K-type thermocouples 156 were supplied to a temperature data acquisition unit 154, and temperature data was averaged and smoothed using a 10-point boxcar averaging scheme.

Equations for Mass Loading and Viscosity-Density Perturbation of BAW Resonators

When using a BAW resonator-type sensor for liquid-based sensing, it is desirable to monitor frequency at a particular phase crossing as a function of time. If the resonator-type sensor is mass loaded by the analyte that is being detected, the resonator frequency will decrease as the mass loading increases, as predicted by the Sauerbrey equation for QCM structures (1959):

$$\Delta f = \frac{-2 f_o^2}{A \sqrt{\rho_q \mu_q}} \Delta m \quad \text{[Equation 1]}$$

where $f_o$=resonant frequency, $\Delta m$=mass change, $A$=piezoelectrically active region, $\rho_q$=density of quartz, and $\mu_q$=shear modulus of quartz.

The liquid supply switching sensor test apparatus 140 illustrated in FIG. 9 uses viscosity•density measurements that perturb the piezoelectric sensor in a manner described by Kanazawa and Gordon for QCM structures (1985):

$$\Delta f = -f_o^{\frac{3}{2}} \sqrt{\frac{\rho_l n_l}{\pi \rho_q \mu_q}} \quad \text{[Equation 2]}$$

where $\rho_l$=density of liquid and $n_l$=viscosity of liquid.

Per Equation 2, the frequency will change by the square root of the viscosity•density product of the liquid contacting the active region of the resonator-type sensor. Utilizing viscosity•density measurements by periodically (and reversibly) altering composition of liquid supplied to a sensor active region provides a convenient means of analyzing a resonator-type sensor over multiple cycles of analyte supplied to the sensor, as compared with most mass-loading phenomena that embody irreversible, one-time events. Use of viscosity•density measurements can help collect statistics on sensor performance and further permit assessment of the measurement system stability over time.

Dependence of Sensitivity on Phase Crossing

Applicant's experimentation utilizing the above-described liquid supply switching sensor test apparatus 140 revealed that the phase crossing that is being monitored determines the sensitivity of a BAW resonator-based sensing device. The sensitivity of a BAW resonator-based sensing device may be calculated as the amount of frequency shift per unit mass added (for mass loading based measurements) or the amount of frequency shift per change in mixture concentration (for viscosity•density measurements, as described herein).

Figure 10:
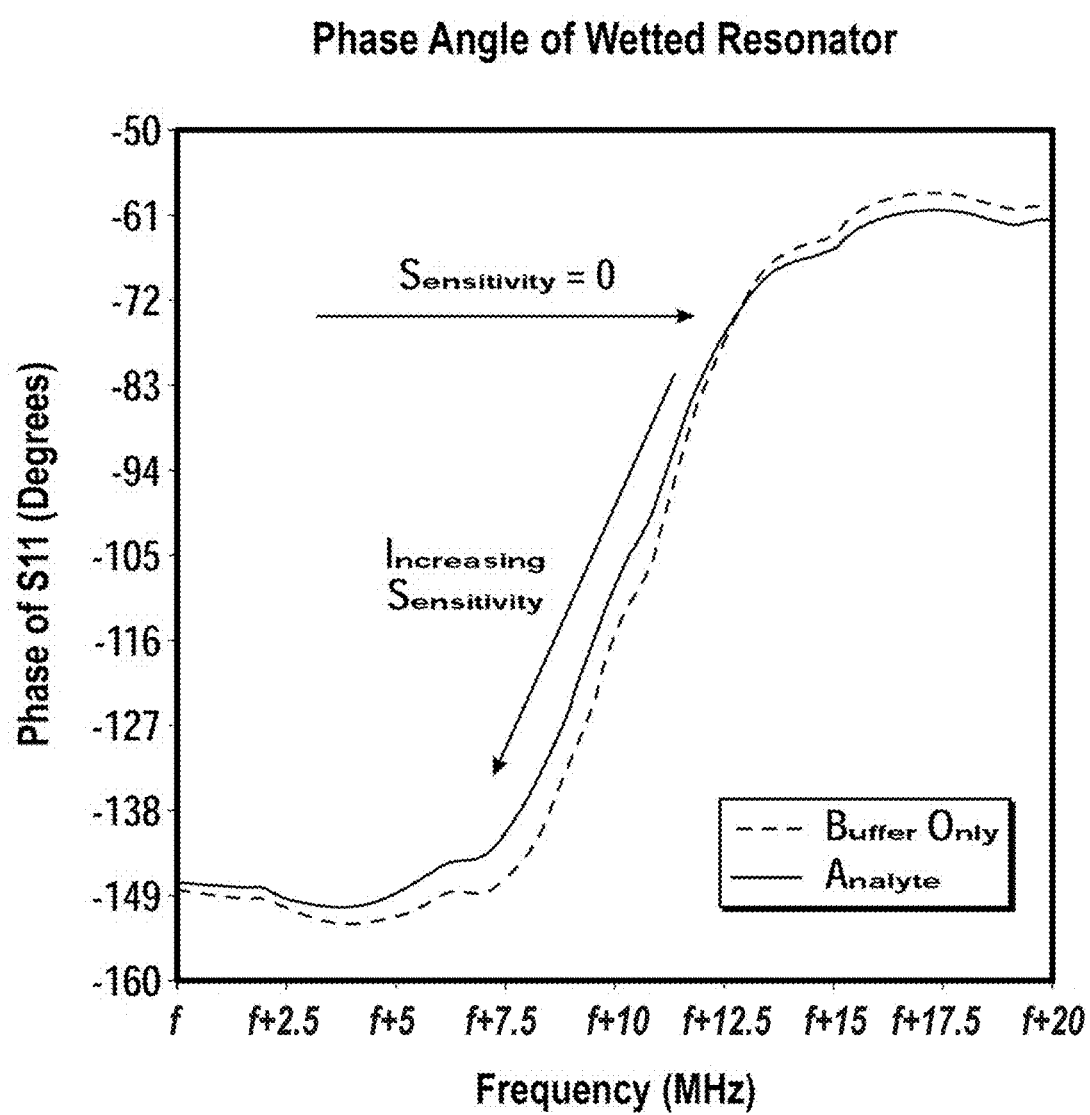
FIG. 10 provides plots of phase of S11 versus frequency for a first BAW resonator wetted with buffer (deionized (DI) water only) and wetted with a glycerine mixture (5% glycerine/DI water), respectively, depicting where the sensitivity goes to zero and how sensitivity increases away from the zero-sensitivity location.

FIG. 10 provides plots of phase of S11 (degrees) versus frequency (MHz) for a first BAW resonator alternately wetted with buffer (deionized (DI) water only) and wetted with a glycerine mixture (5% glycerine/DI water) (e.g., "Analyte"), respectively. An arbitrary frequency f is identified at the origin, with increments of 2.5 MHz along the x-axis. Sensitivity of the BAW resonator at various positions on the phase curve was determined by passing a 0.1% glycerine/DI water mixture over the BAW resonator for a 10-minute interval, alternating between pure DI water and the glycerine/DI water combination, while temperature was kept constant. The two plots exhibit substantially the same shape with relative rotation therebetween at an intersection point corresponding to a phase angle value of about 75°. The intersection point represents the point at which the same frequency is obtained regardless of phase of S11—namely, where the sensitivity (i.e., the amount of frequency shift per change in mixture concentration) is zero. At frequencies move away from the zero sensitivity point (either lower or higher), sensitivity increases.

Figure 11:
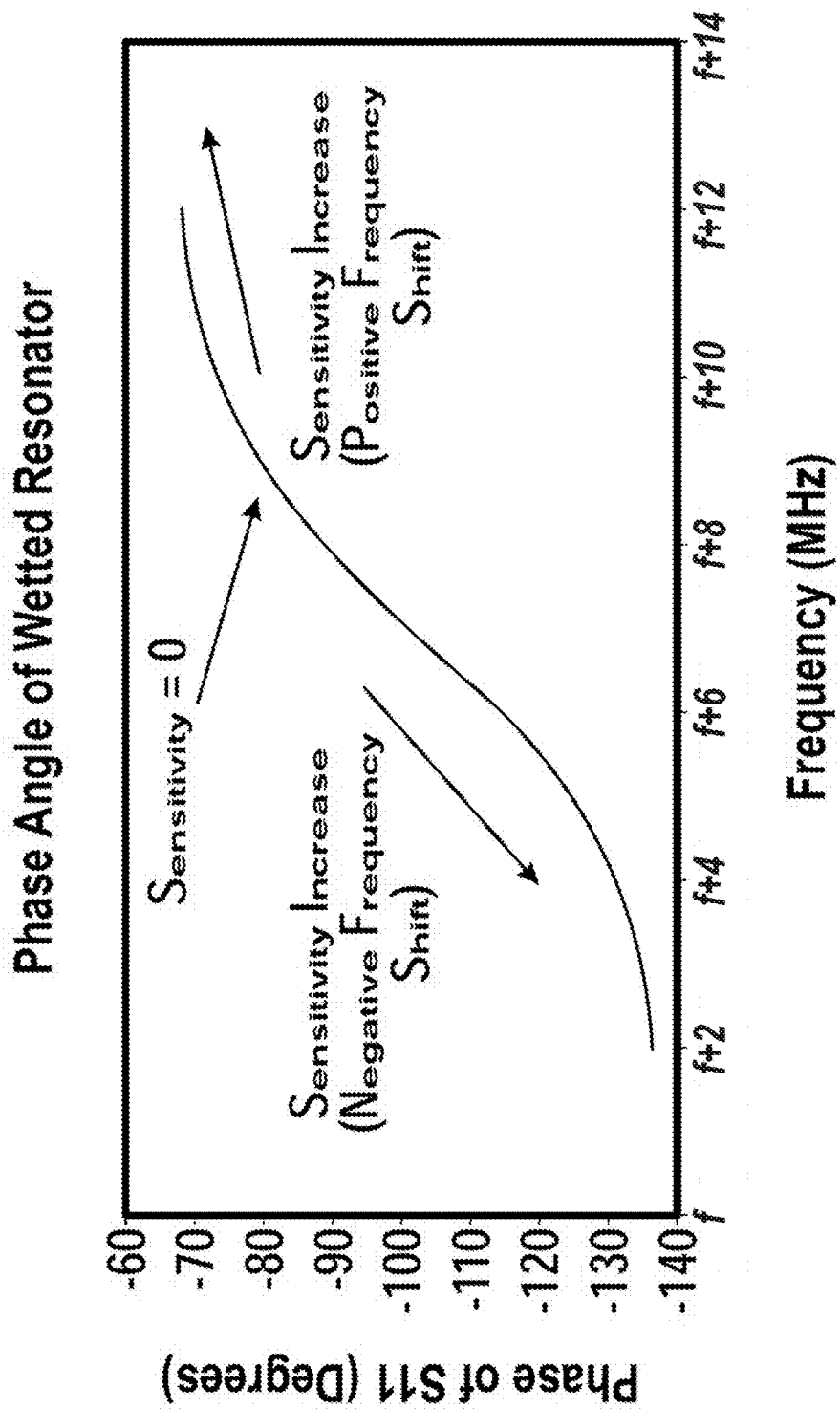
FIG. 11 is a smoothed single plot of phase of S11 versus frequency for a second BAW resonator wetted with a buffer (deionized (DI) water only) and alternately wetted with a glycerine mixture (0.1% glycerine/DI water), depicting where the sensitivity goes to zero (at approximately −80 degrees) and how sensitivity increases away from the zero-sensitivity location.

FIG. 11 is a smoothed single plot of phase of S11 (degrees) versus frequency (MHz) for a second BAW resonator wetted with buffer (deionized (DI) water only) and alternately wetted with a glycerine mixture (0.1% glycerine/

DI water), when operated at (f+6) MHz. An arbitrary frequency f is identified at the origin, with increments of 2 MHz along the x-axis. To determine the sensitivity of the BAW resonator at various positions on the phase curve, a 0.1% glycerine/DI water mixture was passed over the BAW resonator for a 10-minute interval, alternating between pure DI water and the glycerine/DI water combination, while temperature was kept constant. Annotated in the figure are the zero sensitivity point (corresponding to −80 degrees) and arrows depicting how sensitivity increases away from the zero-sensitivity location. At frequencies higher than the zero sensitivity point, response of the BAW resonator is inverted.

Figure 12A:
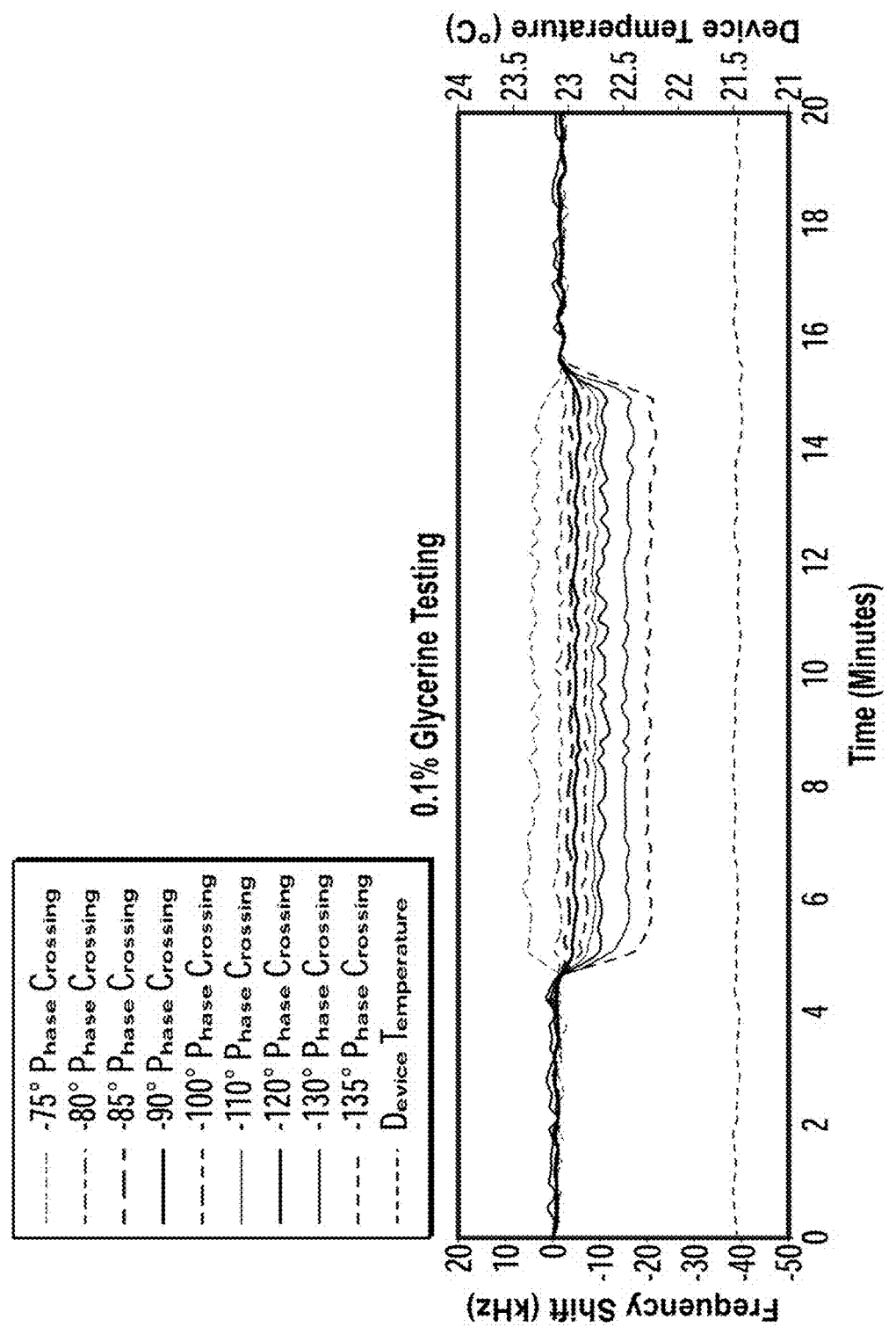
FIG. 12A provides plots of frequency shift as a function of time for a 10-minute glycerine mixture injection (0.1% glycerine/deionized (DI) water) showing different sensitivities at different phase values, including a lack of sensitivity at a −80 degree phase crossing, and increasing sensitivity as the phase angle is made more negative.

FIG. 12A provides plots of frequency shift (kHz) as a function of time (minutes) for a 10-minute glycerine mixture injection (0.1% glycerine/deionized (DI) water) showing different sensitivities of the BAW resonator of FIG. 11 at different phase values. FIG. 12A shows a lack of sensitivity at a −80 degree phase crossing, and increasing sensitivity as the phase crossing angle is made more negative. The −75 degree phase crossing shows an opposite sign in its response. The device temperature is also plotted in FIG. 12A (embodied in the bottom trace), with a value that remained constant during this measurement at 21.5° C.

Frequency shift (kHz) and sensitivity (kHz/% glycerine) values corresponding to the plots shown in FIG. 12A are tabulated in FIG. 12B as a function of phase crossing where the frequency shift is monitored. As shown in the data of FIG. 12B, sensitivity is greatest at the low frequency end of the phase curve, so in general more negative values of the phase crossing should be monitored in order to maximize the signal-to-noise ratio in liquid-based sensor measurements. The sensitivity has an opposite sign, as the frequency is increased above the sensitivity=0 point on the phase curve. The dependence of the sensitivity upon the phase curve is a novel finding in the present disclosure. The phase response toggles around a sensitivity=0 point, where points at higher frequency increase positively in frequency and points at lower frequency decrease in frequency as the viscosity•density product of the analyte increases.

Introduction to α: Temperature Coefficient of Frequency ("TCF")

Using a linear approximation, which is valid for small temperature changes, the temperature dependence of the frequency of a BAW resonator is given as:

$$f(T)=f(T_o)(1+\alpha \Delta T)$$

where $T_o$=the reference temperature, $f(T_o)$=frequency value at the reference temperature, α=the temperature coefficient of frequency=TCF, and $\Delta T=T-T_o$. It was determined empirically that the TCF (i.e., α) can be either positive or negative depending upon the angle of the phase crossing being monitored.

Figure 13:
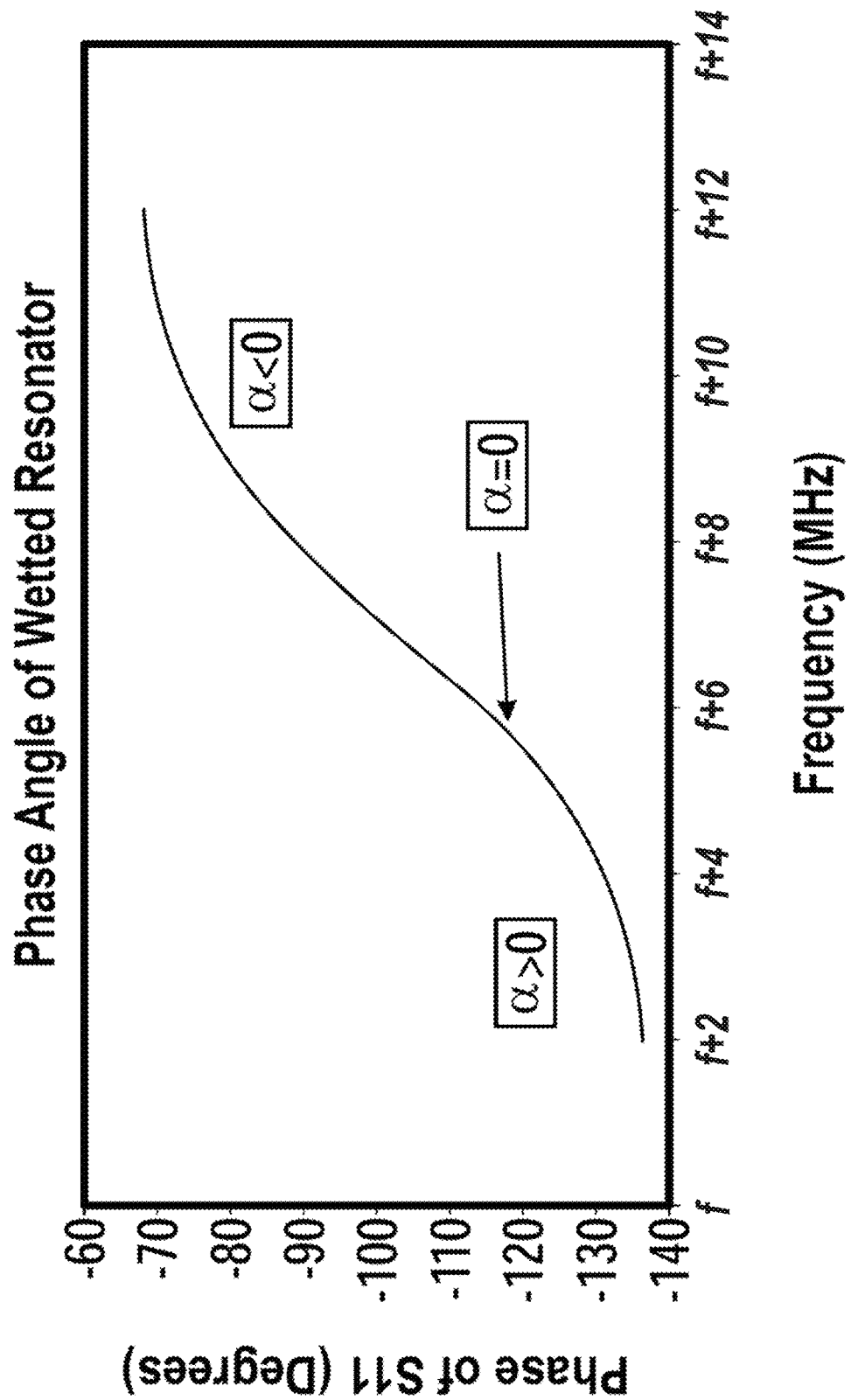
FIG. 13 is a phase plot (phase of S11 versus frequency) for a wetted BAW resonator depicting where the temperature coefficient of frequency (TCF, or α) goes through 0, with positive and negative values on either side of this operating point.

FIG. 13 is a phase plot (phase of S11 (degrees) versus frequency (MHz)) for a wetted BAW resonator operated at (f+6) MHz, depicting where the temperature coefficient of frequency (TCF, or α) goes through zero, with positive and negative values on either side of this operating point. An arbitrary frequency f is identified at the origin, with increments of 2 MHz along the x-axis. At less negative phase angles, the TCF is negative and actually goes through zero as the phase angle is incremented to more negative values. Beyond this critical phase angle, where the TCF is zero, the coefficient becomes positive. These three areas of operation are depicted in FIG. 13.

Figure 14A:
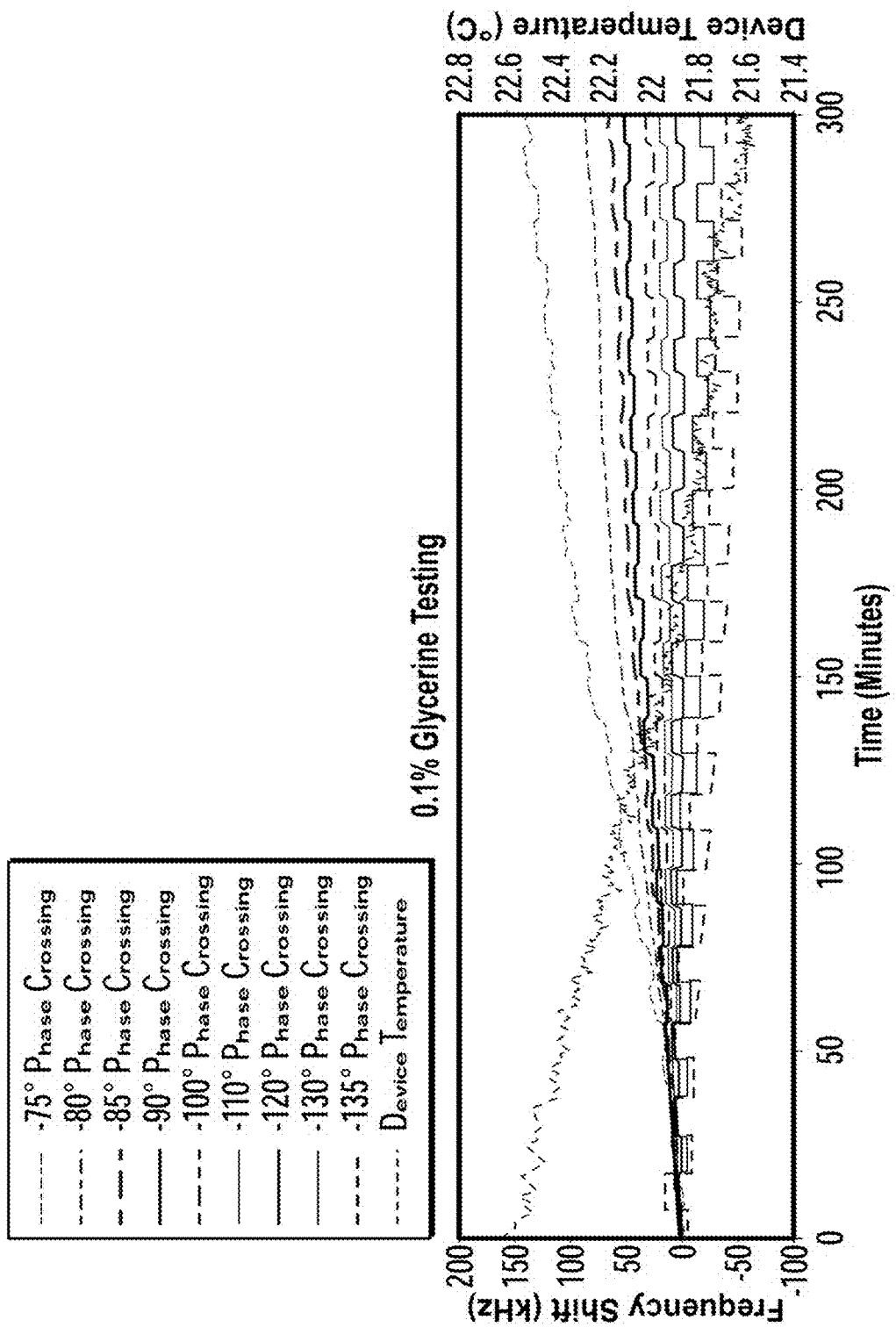
FIG. 14A provides plots of frequency shift as a function of time for multiple 10-minute glycerine mixture injections (0.1% glycerine/deionized (DI) water) for a wetted BAW resonator for nine investigated phase crossing values, with superimposed device temperature.

FIG. 14A provides plots of frequency shift (kHz) as a function of time (minutes) for multiple 10-minute glycerine mixture injections (0.1% glycerine/deionized (DI) water) for a wetted BAW resonator for nine investigated phase crossing values, with superimposed device temperature. The change in TCF as a function of phase crossing is apparent. The device temperature (plot starting at upper left) changes by about one degree Celsius over the course of time shown in FIG. 14A. As shown in FIG. 14A the data for phase angles more negative than −120 degrees show a positive TCF. The −120 degree data show the least amount of temperature sensitivity, and TCF is negative for phase angles more positive than −120 degrees.

Figure 14B:
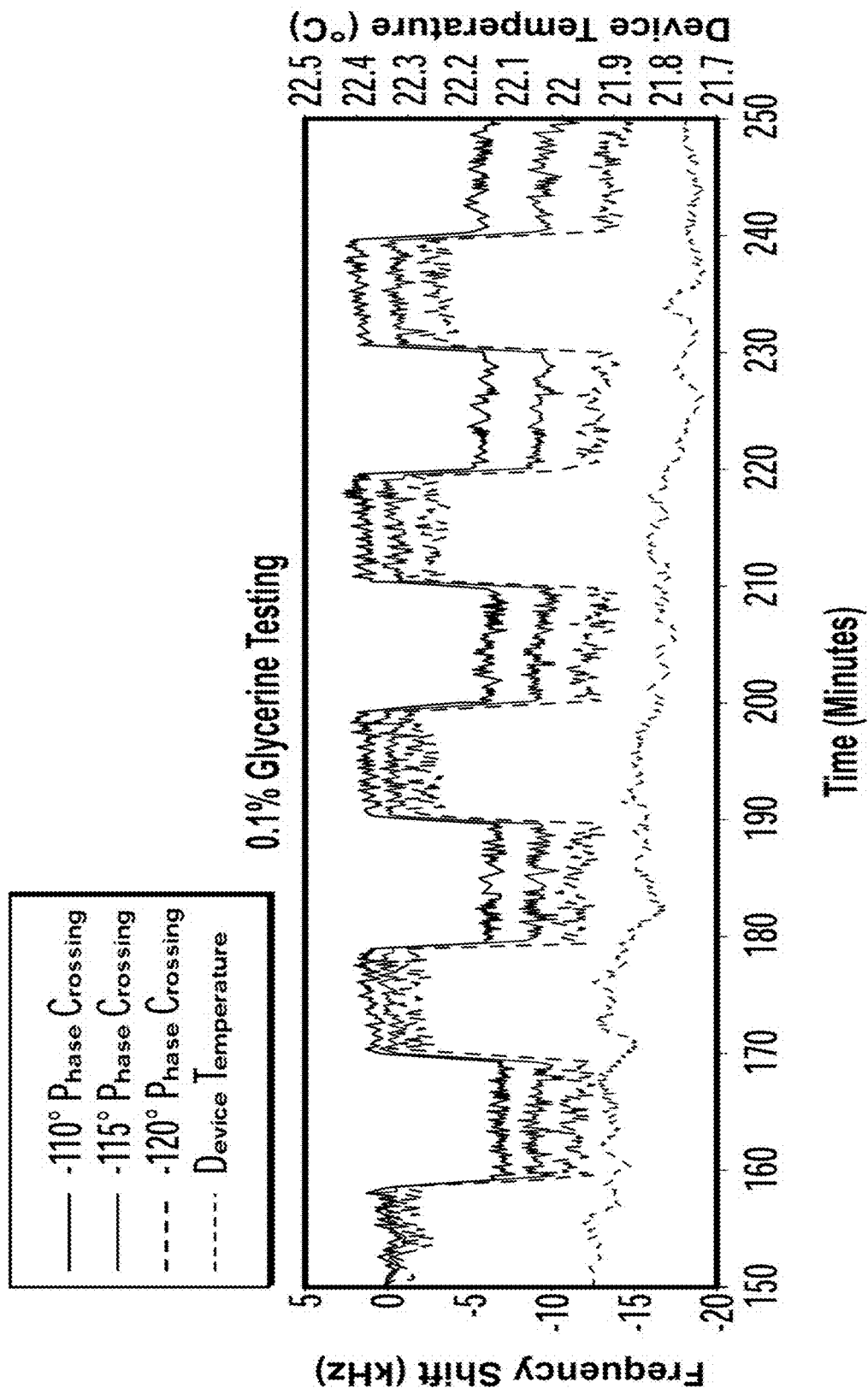
FIG. 14B is a magnified portion of a subset of FIG. 14A, providing plots of frequency shift as a function of time for five 10-minute glycerine mixture injections (0.1% glycerine/deionized (DI) water) for the wetted BAW resonator for three investigated phase crossing values, with superimposed device temperature.

FIG. 14B is a magnified portion of a subset of FIG. 14A (from 150 to 250 minutes), providing plots of frequency shift (kHz) as a function of time (minutes) for five 10-minute glycerine mixture injections (0.1% glycerine/deionized (DI) water) for the wetted BAW resonator for three investigated phase crossing values, with superimposed device temperature. The three phase crossing values are all near the TCF (or α)=0 point, providing further refinement of the phase regime in which the sensor response will have the lowest temperature sensitivity. The data at the −120 degree phase crossing show a slightly positive TCF. The data at the −115 degree phase crossing show the least amount of temperature sensitivity (TCF=0), and the data at the −110 degree phase crossing are negative. The change in device temperature is approximately 0.2 degrees for this data set.

Figures 15, 16:
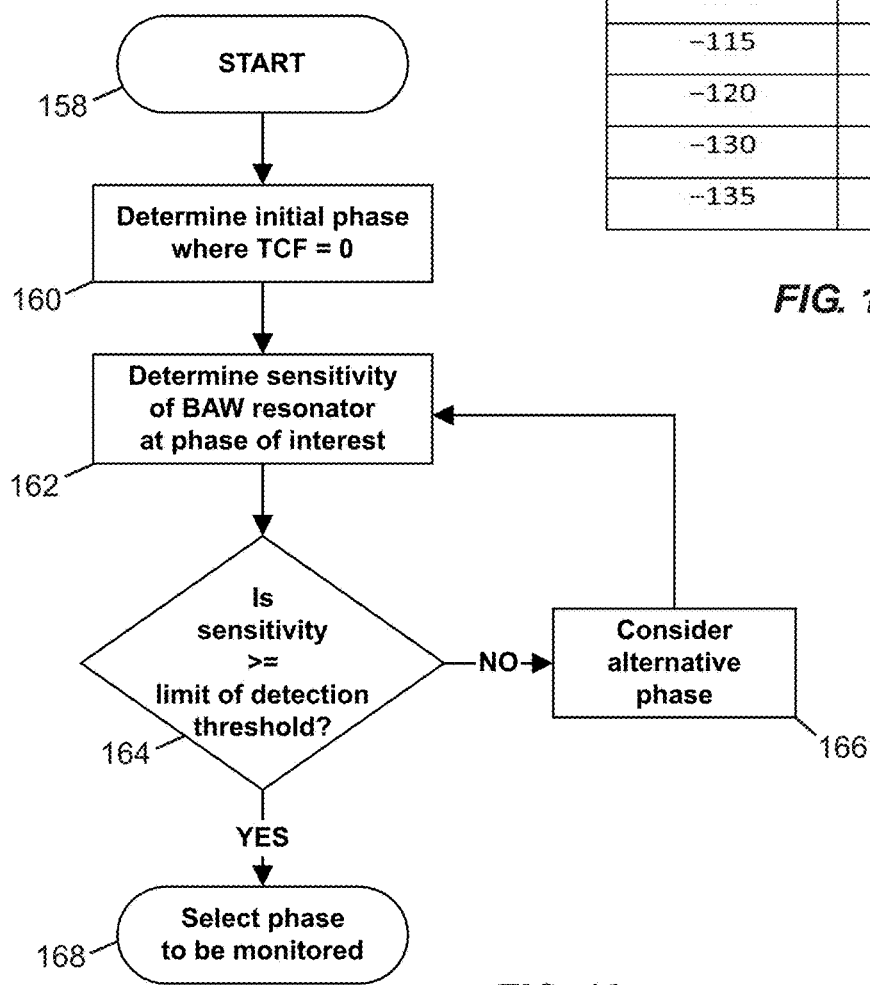
FIG. 15 is a table identifying temperature coefficient of frequency (TCF, also represented as α) calculated for ten phase crossing values investigated in connection with FIGS. 14A and 14B.
FIG. 16 is a flowchart depicting steps of a method for configuring operation of a BAW resonator by determining a phase of the BAW resonator to be monitored over time to provide suitable sensitivity in combination with reduced effect of temperature on measurement accuracy (e.g., enhanced immunity to temperature drift), according to one embodiment.

FIG. 15 shows the calculated TCF as a function of ten phase crossings monitored in connection with FIGS. 14A and 14B. As shown, the BAW resonator has the lowest amount of temperature sensitivity (i.e., TCF=0 (α=0)) at a phase crossing value of −115 degrees.

Determination of Phase to be Monitored to Provide Suitable Sensitivity in Combination with Reduced Effect of Temperature on Measurement Accuracy Use of the operation point where TCF=0 (α=0) on the phase curve is believed to be a novel finding of the present disclosure, and represents a condition where BAW resonator measurements can be made with the best immunity to temperature drift. It is noted that a dry resonator will typically have a negative TCF around its resonance, but for the case of liquid-based operation of a BAW resonator, the TCF is positive in the area of interest (i.e., area of maximum sensitivity).

If the operation point (i.e., phase crossing) of a BAW resonator where TCF=0 (α=0) exhibits sufficiently high sensitivity for a phenomenon of interest relative to a limit of detection threshold of the BAW resonator for the same phenomenon of interest, then the same operating point (i.e., phase crossing where TCF=0) may advantageously be monitored to provide the best immunity to temperature drift. Conversely, if the phase crossing value where TCF=0 does not exhibit sensitivity greater than a limit of detection threshold for the phenomenon of interest, then a phase crossing value may be incremented to an alternative value, sensitivity of the BAW resonator for the phenomenon of interest at the alternative phase may be determined, and this sensitivity may be compared to the limit of detection threshold. The process may be continued with additional phase crossing values until the sensitivity is determined to exceed the limit of detection threshold.

FIG. 16 is a flowchart depicting steps of a method for configuring operation of a BAW resonator by determining a phase of a BAW resonator to be monitored over time to provide suitable sensitivity in combination with reduced effect of temperature on measurement accuracy (e.g., enhanced immunity to temperature drift), according to one embodiment. A starting block 158 is provided. Block 160 includes a step of determining an initial phase (e.g., phase crossing value) where the temperature coefficient of frequency (TCF) value is substantially equal to zero. Such value represents a condition where BAW resonator measurements can be made with the best immunity to temperature drift. Referring to block 162, sensitivity of the BAW resonator to a phenomenon of interest at the phase (phase crossing value) being evaluated (i.e., "phase of interest") is determined. Referring to block 164, the determined sensitivity is compared to a limit of detection threshold for the same phenomenon of interest. If the determined sensitivity is greater than or equal to the limit of detection threshold, then the phase being evaluated (e.g., the initial phase) is selected to be monitored during operation of the BAW resonator (block 168). Conversely, referring to block 164, if the determined sensitivity is not greater than or equal to the limit of detection threshold, then an alternative phase is considered (block 166), such as by incrementing the phase in a direction intended to increase measurement sensitivity (e.g., by selecting a more negative phase than the initial phase), and the method returns to block 162 to determine sensitivity of the BAW resonator at the (new) phase of interest. Thereafter, the method proceeds to block 164, whereby the determined sensitivity is compared to a limit of detection threshold for the same phenomenon of interest, and the process may be continued until the determined sensitivity exceeds or equals the limit of detection threshold for the phenomenon of interest. The resulting phase (phase crossing value) is then selected to be monitored during operation of the BAW resonator, to enable operation of the BAW resonator with maximum sensitivity for a phenomenon of interest and minimum temperature dependence.

In certain embodiments, the phenomenon of interest may include one or more of pressure in an environment containing an active region of the BAW resonator, binding of mass on or over an active region of the BAW resonator, density of a fluid medium arranged on or over an active region of the BAW resonator, or viscosity of a fluid medium arranged on or over an active region of the BAW resonator. In certain embodiments, the foregoing method for configuring operation of a BAW resonator may be used in combination with a temperature compensation method as further disclosed herein.

Introduction to Conventional Temperature Compensation Methods

Figure 17A:
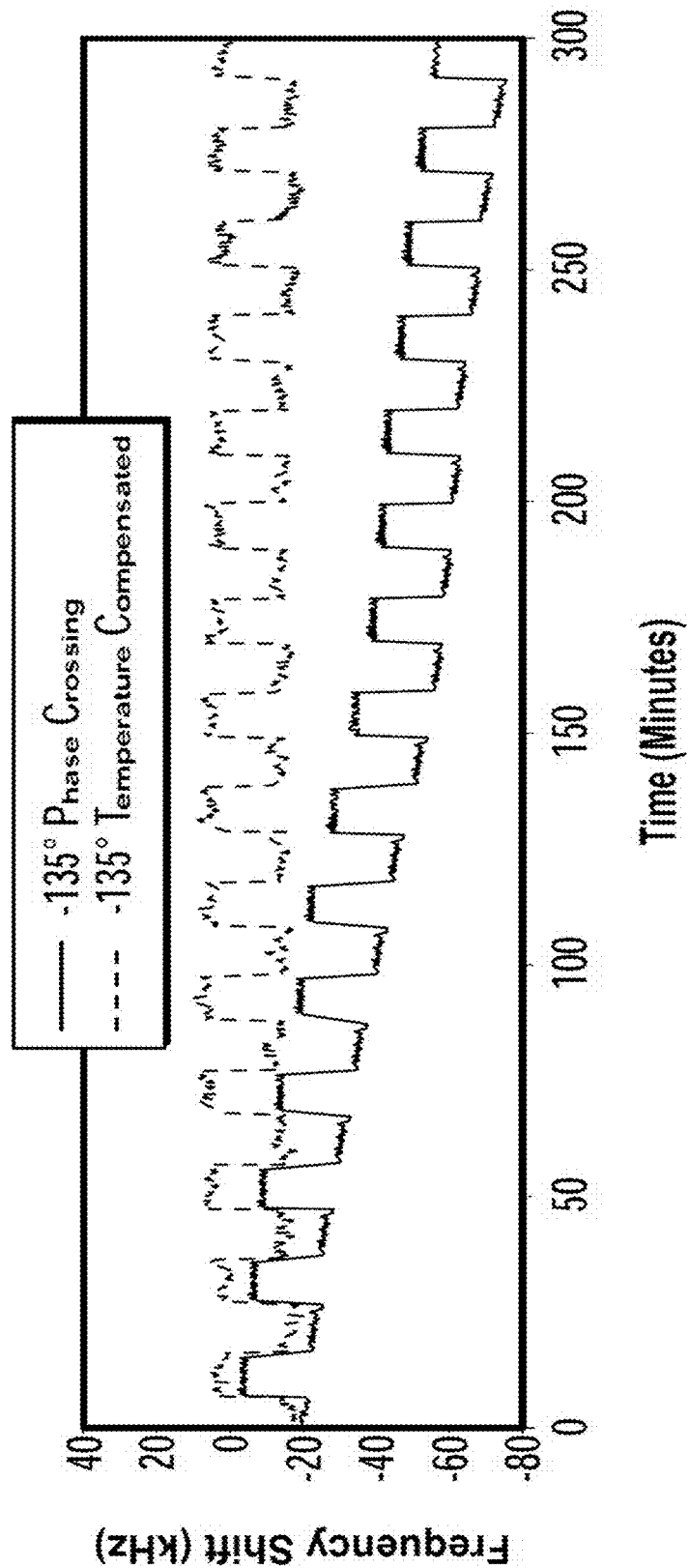
FIG. 17A includes plots of frequency shift versus time for raw data and conventionally temperature-compensated data for multiple glycerine mixture injections (0.1% glycerine/DI water) across a BAW resonator obtained using the −135° phase crossing.

Since the linear TCF can be determined if the temperature of the device is known, applying a simple linear correction to any data for which TCF (or α)≠0 is straightforward. An example of this is shown in FIG. 17A, which includes plots of frequency shift (kHz) versus time (minutes) for raw data and conventionally temperature-compensated data for multiple glycerine mixture injections (0.1% glycerine/DI water) across a BAW resonator obtained using the −135° phase crossing. The data taken at the −135 degree phase crossing have been temperature compensated in a conventional manner using the actual device temperature. As shown, the raw data exhibits a distinct frequency shift with respect to time, whereas the temperature corrected data is free of any significant frequency shift. It is noted that the noise present in the temperature data (from a temperature sensor output signal) is replicated in the temperature-compensated data when this conventional approach is used, thereby resulting in degradation of signal-to-noise ratio. The noise in the temperature data can be seen in the plot of FIG. 17A.

The temperature noise visible in FIG. 17A can be reduced by taking a linear fit of the temperature data with time, but this approach further complicates the simple compensation algorithm. The data in FIG. 17B was generated using this approach and results in a better signal-to-noise ratio than using the real device temperature at each instance in time (as shown by comparison of FIGS. 17A and 17B).

Figure 17B:
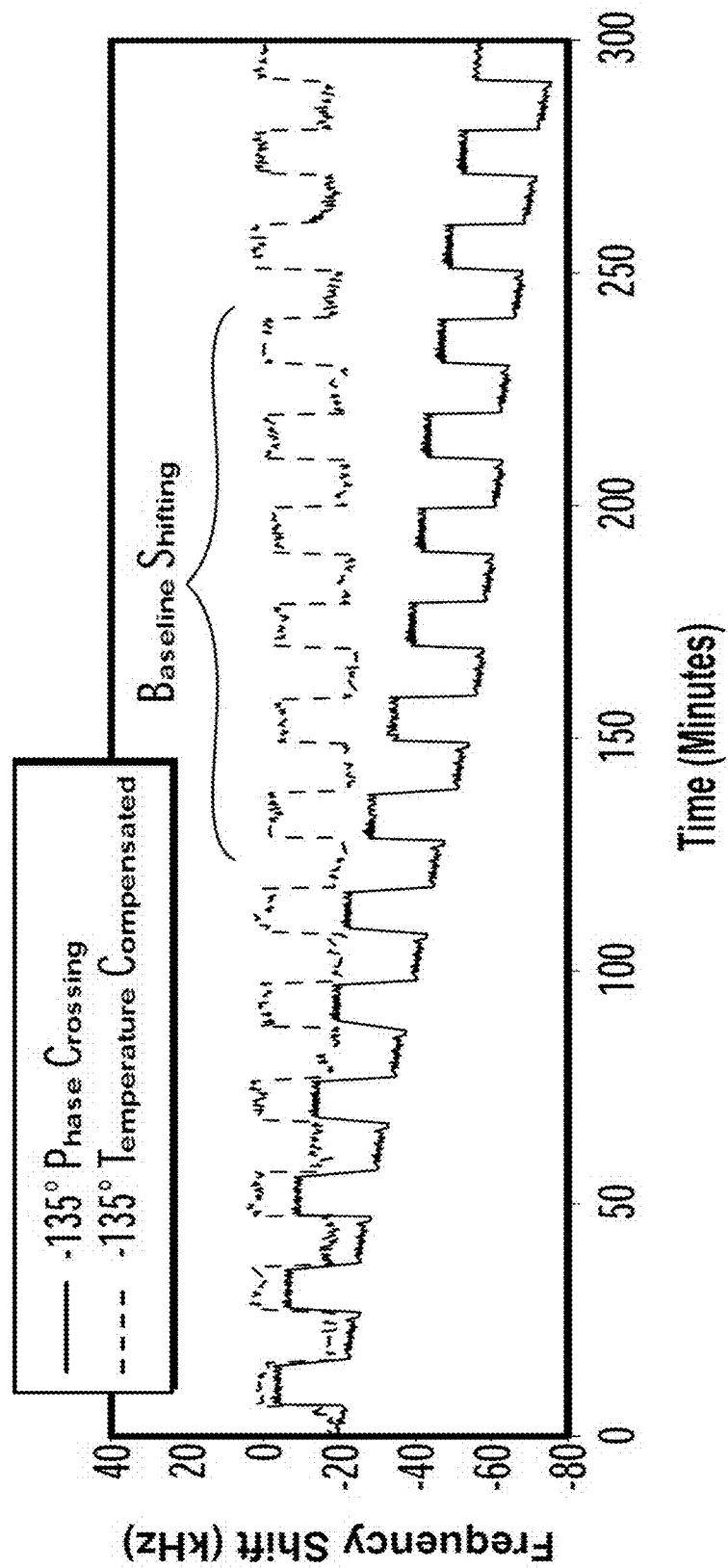
FIG. 17B includes plots of frequency shift versus time for raw data and temperature-compensated data for multiple glycerine mixture injections (0.1% glycerine/DI water) across a BAW resonator obtained using the −135° phase crossing and taking a linear fit of the temperature data with time to reduce noise.

FIG. 17B includes plots of frequency shift versus time for raw data and temperature-compensated data for multiple glycerine mixture injections (0.1% glycerine/DI water) across a BAW resonator obtained using the −135° phase crossing and taking a linear fit of the temperature data with time to reduce noise. The technique used in FIG. 17B results in lower noise, but the baseline does exhibit shifting as a function of time, as labeled in FIG. 17B. This (e.g., downward) shifting is a result of when the error of the linear fit of the temperature data increases. Overall, utilization of a linear fit of the temperature data with time represents a decent compensation technique when the measurement can allow linearization of the temperature data. This technique can be more cumbersome, however, when the slope of the temperature with time (ΔT/Δt) changes rapidly.

Novel Temperature Compensation Methods not Requiring Sensing of Temperature or Obtaining a Reference Temperature The following temperature compensation technique embodies an improvement over conventional methods because it does not require measurement of temperature of a BAW resonator during the BAW sensing operation, and does not necessitate obtaining of a reference temperature. This technique relies on the linear temperature dependence of the BAW resonator itself over the small changes in temperature that the BAW resonator will experience.

Briefly, a phase angle is determined in which temperature is correlated with a particular phase angle. A relationship is determined between the frequency shift at this phase angle and the frequency shift at the phase angle where the measurement will be conducted. Upon obtaining a raw S-parameter response signal from a BAW resonator, such signal may be temperature corrected using a relationship between (i) change in frequency of the BAW resonator at a phase with adequate sensitivity and (ii) change in frequency of a phase that is correlated to temperature.

Figure 18:
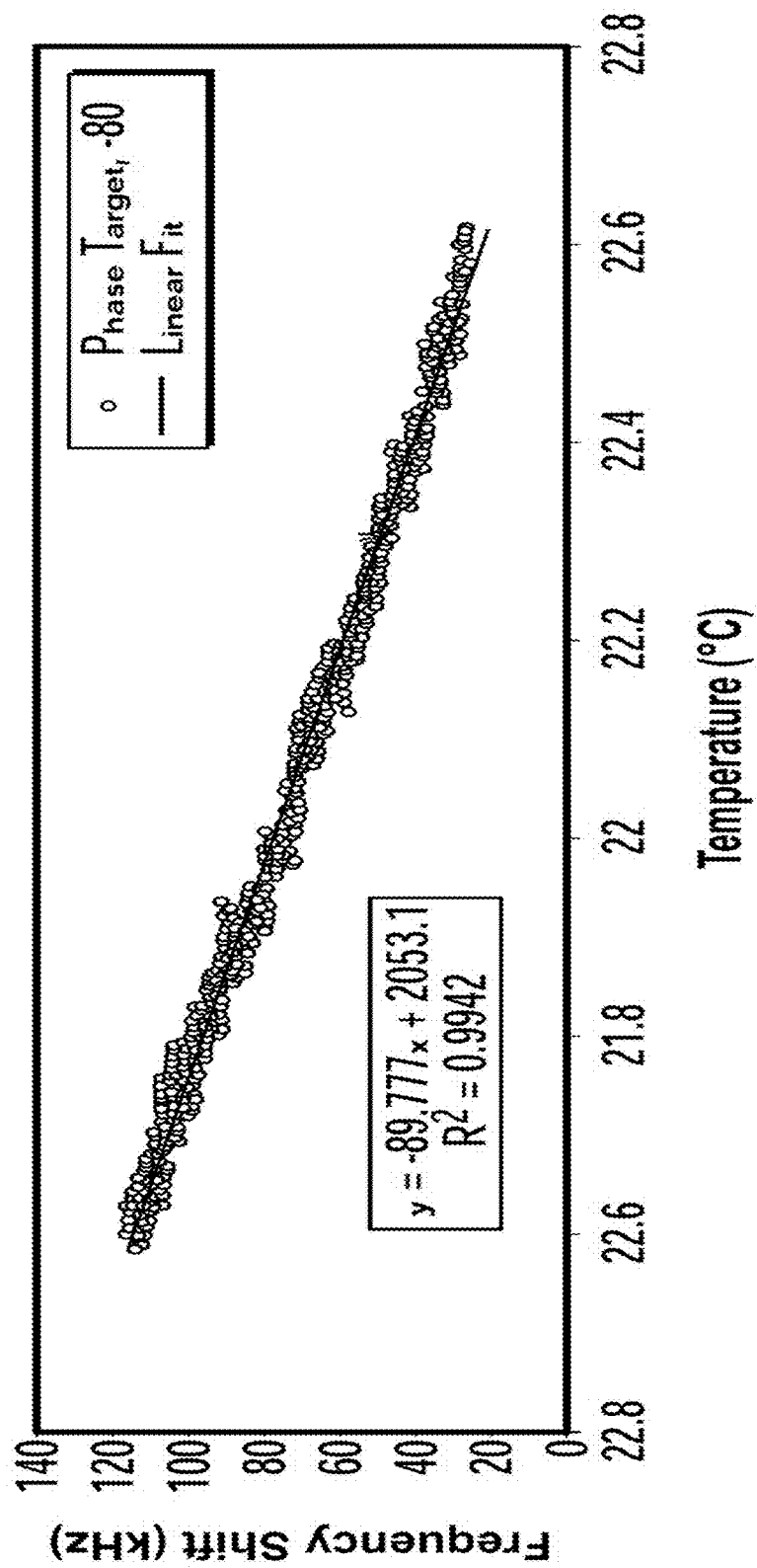
FIG. 18 is a plot of −80° phase crossing frequency shift as a function of temperature with a superimposed linear fit for multiple glycerine mixture injections (0.1% glycerine/DI water) across a BAW resonator.

FIG. 18 is a plot of −80° phase target crossing frequency shift (kHz) as a function of temperature, with a superimposed linear fit, for multiple glycerine mixture injections (0.1% glycerine, D1 water) across a BAW resonator. The data are well correlated and provide a substantial change in frequency (~100 kHz) for a small change in temperature (~1° C.), making the −80° phase target crossing value a good temperature monitor.

Since there is a very strong correlation in the data ($R^2$=0.9942), the phase crossing itself can be used as the independent variable in the compensation algorithm instead of the device temperature. In effect, the phase crossing that has sufficiently high TCF (either positive or negative) is used as the temperature reading. In determining a phase angle where temperature is well-correlated, it is noted that the phases that are more sensitive to temperature occur on the region of the phase (frequency) relationship (see FIG. 13) where TCF>0, corresponding to lower phase angles. In the analysis to follow, the −80° C. phase crossing was used, but any number of phase crossings with sufficiently high TCF could be used as the independent variable in the algorithm.

A new coefficient, β, is defined as the change in phase crossing frequency at the sensor's phase crossing with respect to another phase crossing value (the one correlated with temperature) having a different TCF:

$$\beta = \frac{\Delta \text{ frequency of sensor at phase crossing with adequate sensitivity}}{\Delta \text{ frequency of phase crossing correlated to temperature}}$$

Restated, a phase where temperature is well correlated with the particular phase may be referred to as $\varphi_2$, and a frequency shift at this point may be referred to as $\Delta f_{\varphi_2}$. The linear relationship between the frequency shift ($\Delta f_{\varphi_2}$) at this phase angle ($\varphi_2$) and the frequency shift ($\Delta f_{\varphi_1}$) at the phase angle ($\varphi_1$) where the measurement will be conducted is determined. The slope in this linear relationship is:

$$\beta = \frac{\Delta f_{\varphi_1}}{\Delta f_{\varphi_2}}$$

Figure 19:
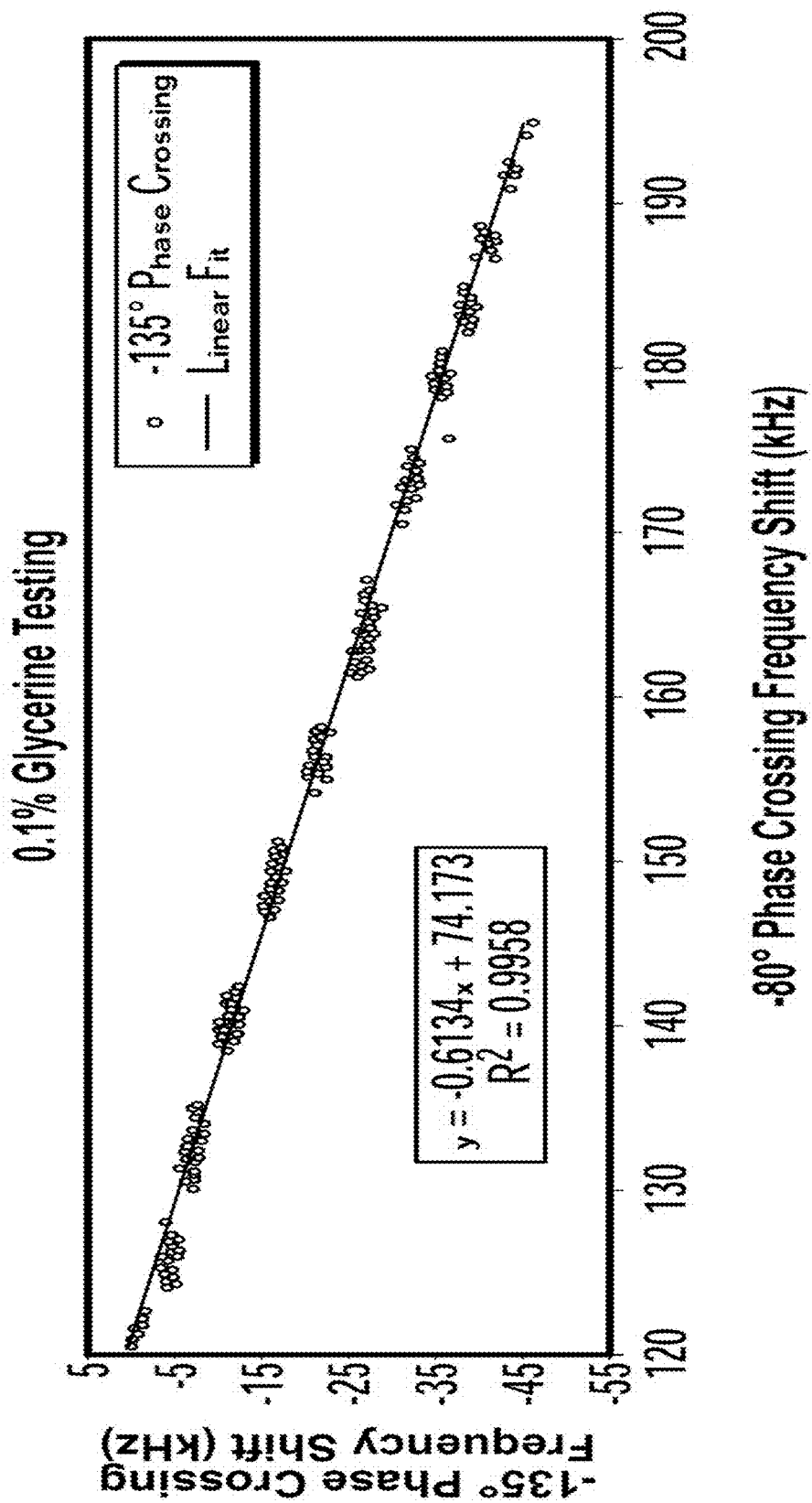
FIG. 19 is a plot of −135° phase target crossing frequency shift as a function of −80° phase crossing frequency shift with a superimposed linear fit for multiple glycerine mixture injections (0.1% glycerine/DI water) across a BAW resonator, wherein the slope of the linear relationship embodies the term β (equaling 0.6134) useable in a temperature compensation method according to one embodiment.

FIG. 19 is a plot of $-135°$ phase crossing frequency shift (i.e., $\Delta f_o$) as a function of $-80°$ phase crossing frequency shift (i.e., $\Delta f_{\varphi_2}$) with a superimposed linear fit for multiple glycerine mixture injections (0.1% glycerine, DI water) across a BAW resonator, wherein the slope of the linear relationship embodies the term β (equaling 0.6134) useable in a temperature compensation method according to one embodiment.

After β is calculated, it can be used to correct for the change in temperature according to the following formula:

Temperature compensated frequency data=$f_{\varphi_1} - \beta * f_{\varphi_2}$

Optionally, an arbitrary offset can be added to the foregoing equation to move the compensated data up or down on the vertical axis, such as by making the frequency shift equal to zero at time=0.

By compensating the response of a BAW resonator with respect to β in the same manner in which the related art used α, the effect is to reduce drift caused by temperature change. This method is advantageous in that there is correlation in some of the noise and drift between the frequency data at the different phase crossings used in the calculations, thereby resulting in good signal-to-noise ratio and reduced baseline drift.

Figure 20:
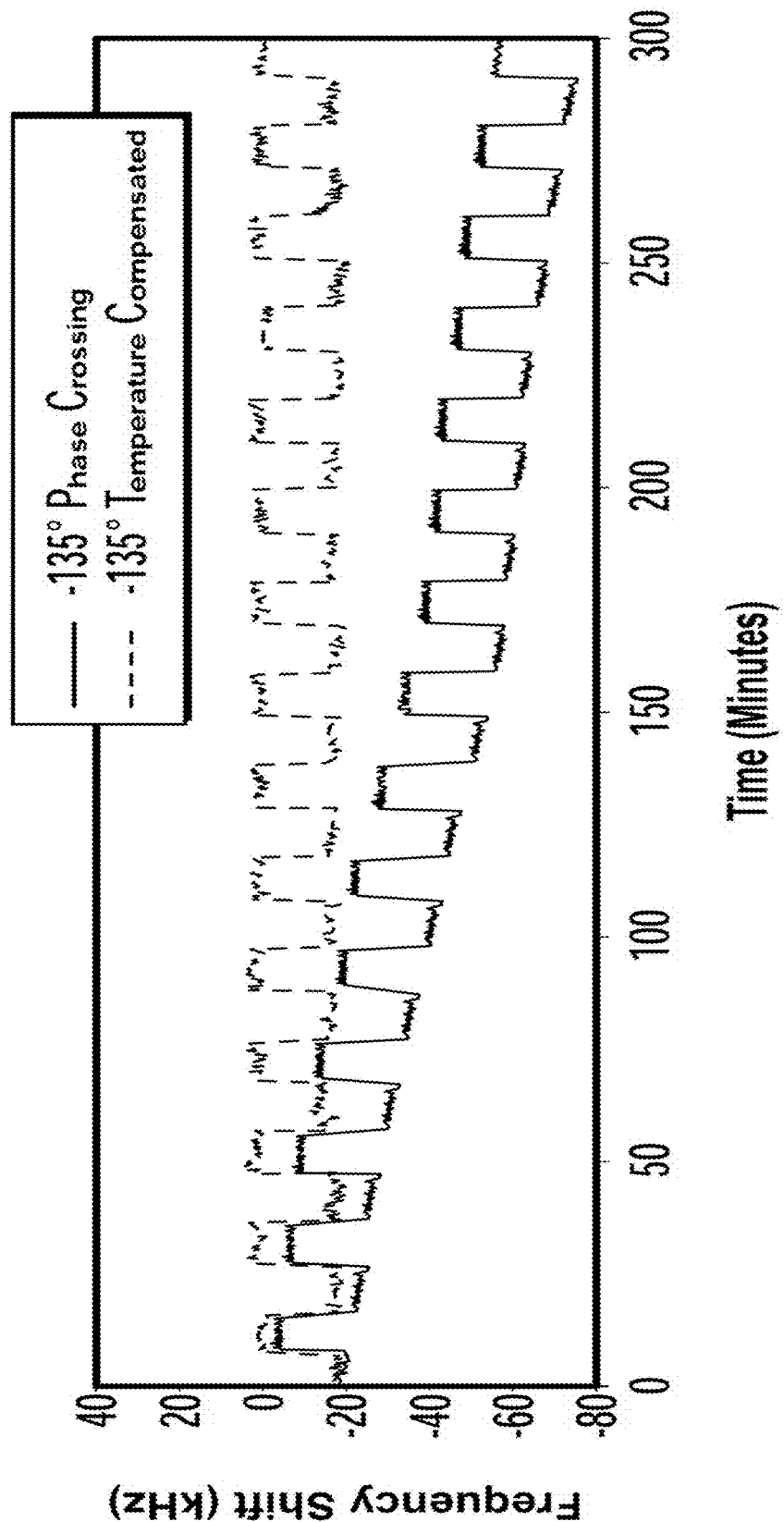
FIG. 20 is a plot of −135° phase crossing frequency shift versus time for raw data and β-method temperature-compensated data for multiple glycerine mixture injections (0.1% glycerine/DI water) across a BAW resonator.

FIG. 20 is a plot of $-135°$ phase crossing frequency shift (kHz) versus time (minutes) for raw data and β method temperature-compensated (e.g., "$-135°$ Temperature Compensated") data for multiple glycerine mixture injections (0.1% glycerine/DI water) across a BAW resonator. As shown in FIG. 20, the β method results in good signal-to-noise ratio and minimal baseline drift.

The TCF=0 (or α=0) point of operation that was discussed previously herein can be determined in a similar manner using the condition that β=0. The point of operation with minimal temperature variation can be found in this manner without actually knowing the device temperature.

FIG. 21 is a table of the calculated β values found in the data set for multiple investigated phase crossing values. Similar to the method involving α, the phase crossing where β=0 is around −115 degrees (as evidenced by the shift from positive to negative values between phase crossing values of −110 and −120 degrees).

Figure 22A:
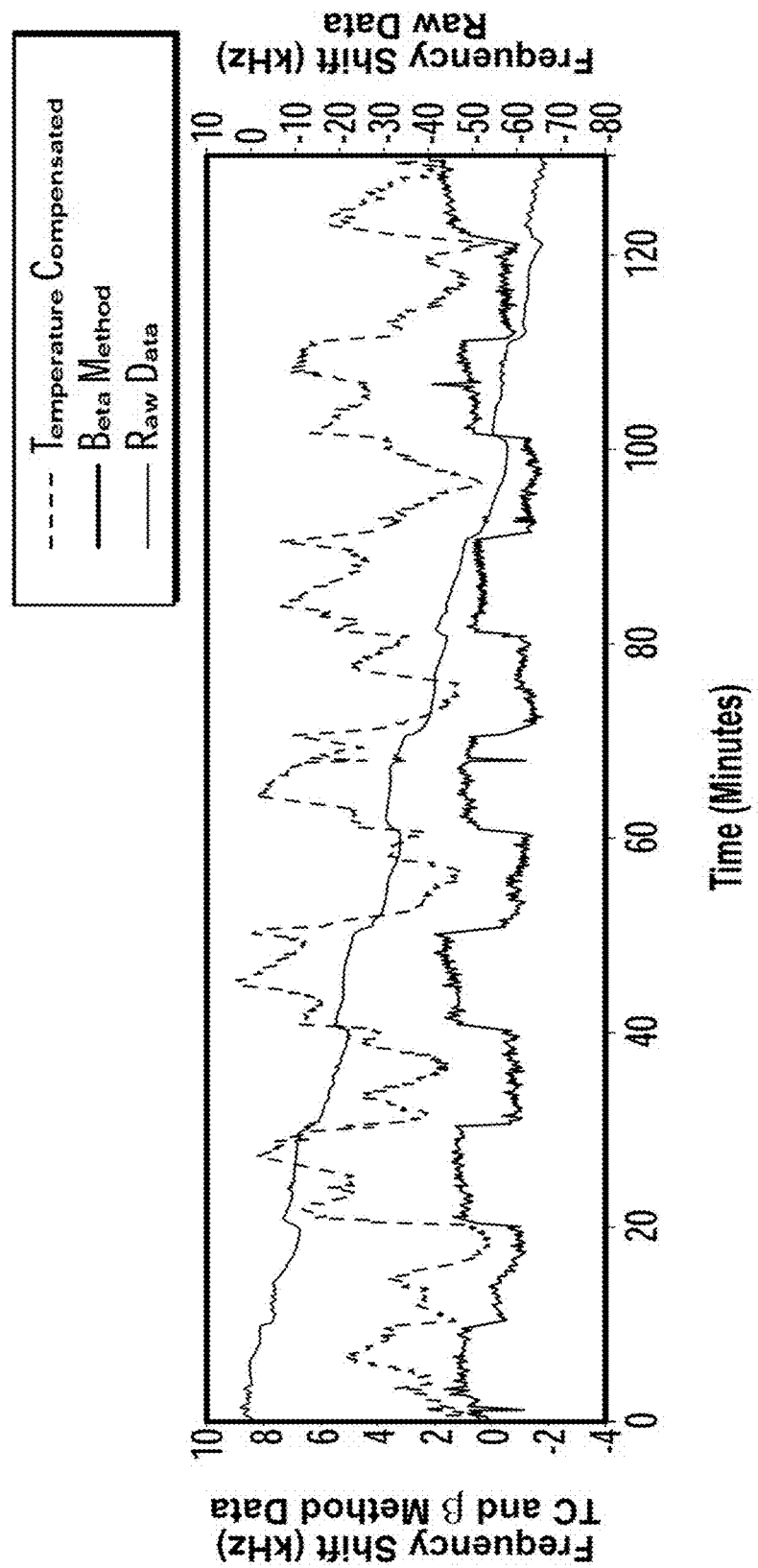
FIG. 22A provides superimposed plots of frequency shift versus time for (i) conventionally temperature compensated data, (ii) β method temperature-compensated data, and (iii) raw data, corresponding to multiple glycerine mixture injections (0.01% glycerine/DI water) across a BAW resonator.
Figure 22B:
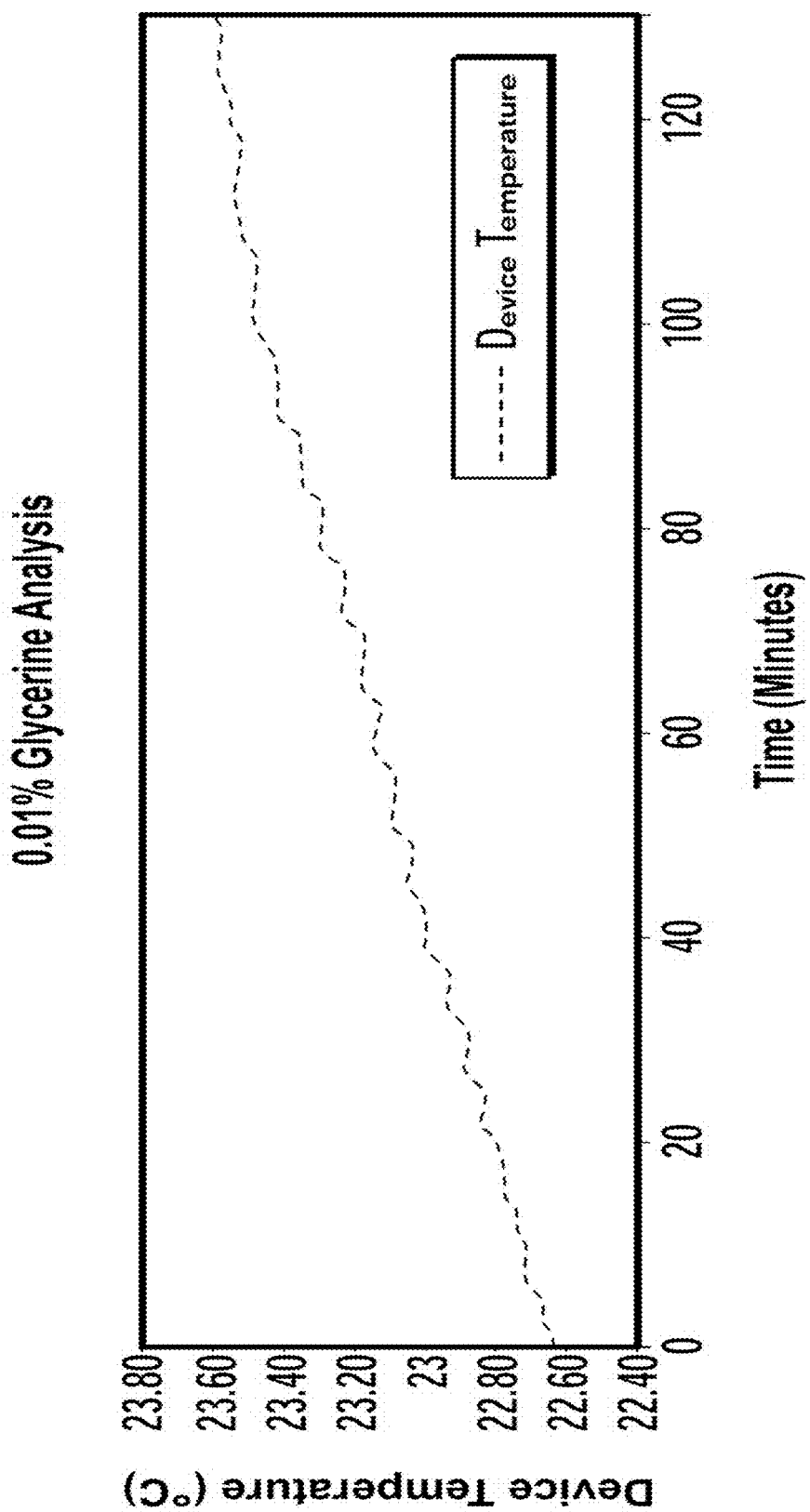
FIG. 22B is a plot of device temperature versus time for the same time period depicted in FIG. 22A.

Applicant's novel temperature compensation method (e.g., β method as outlined above) is particularly advantageous to compensate for sensor signals with very poor signal-to-noise ratios. FIG. 22A provides superimposed plots of frequency shift (kHz) versus time (minutes) for (i) conventionally temperature compensated data, (ii) β method temperature-compensated data ("Beta-method"), and (iii) raw data, corresponding to multiple glycerine mixture injections across a resonator utilizing different technology than the previous data, with a lower glycerine-to-water concentration (0.01%). The device temperature change experienced over the same time period (totaling approximately 1° C.) is shown in FIG. 22B. Referring to FIG. 22A, the raw data (thin solid line) shifts by −70 kHz during the measurement, and the temperature-compensated data (dashed line) are very noisy. Using the β method, a 2 kHz change in signal is readily detected (thick solid line in FIG. 22A).

Numerous technical benefits are provided by Applicant's novel temperature compensation method (β method). Measurement system hardware is simplified by dispensing with the need for temperature measurement hardware (temperature sensor on die or close to die and instrumentation) and the need for a temperature reference device. Good signal-to-noise ratios are provided, and minimal baseline drift is attained. A further benefit is increase of speed of data collection, since data may be taken at two phase crossings with minimal time delay. Additionally, the method can be used to compensate for temperature effects even when the temperature is not known.

It is further noted that the temperature compensation methods disclosed herein can be incorporated into established signal-processing techniques to increase the signal-to-noise ratios for low level signals in noisy environments.

Figure 23:
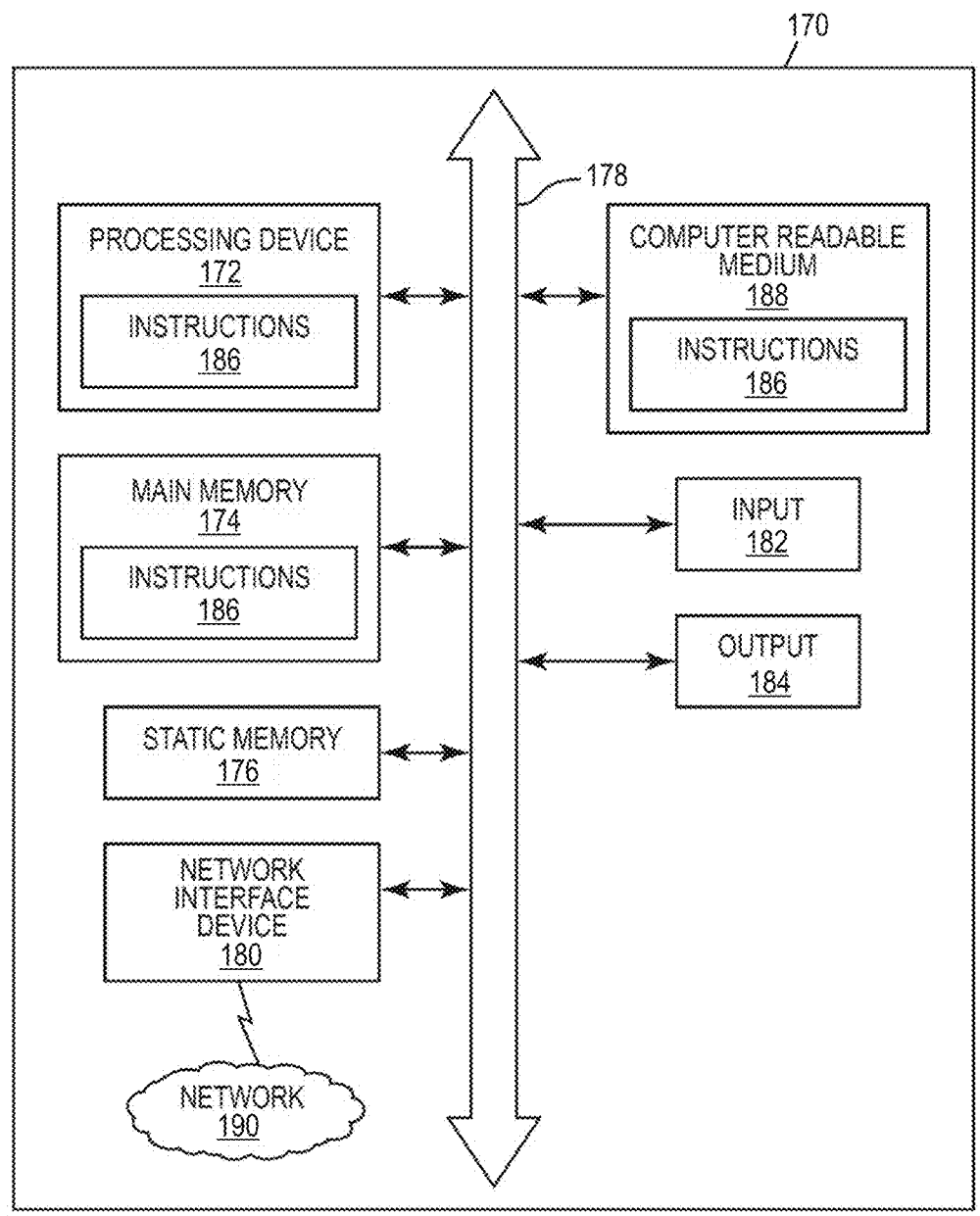
FIG. 23 is a schematic diagram of a generalized representation of a computer system that can be included in any component in a BAW resonator sensing system and/or a BAW resonator operation configuration system and is suitable for performing steps of temperature compensation and/or operational configuration methods as disclosed herein, according to one embodiment.

FIG. 23 is a schematic diagram of a generalized representation of a computer system 170 that can be included in any component in a bulk acoustic wave (BAW) resonator sensing system and/or a BAW resonator operation configuration system suitable for executing method steps disclosed herein, according to one embodiment. In this regard, the computer system 170 is adapted to execute instructions from a computer-readable medium to perform these and/or any of the functions or processing described herein.

In this regard, the computer system 170 in FIG. 23 may include a set of instructions that may be executed to program and configure programmable digital signal processing circuits for supporting scaling of supported communications services. The computer system 170 may be connected (e.g., networked) to other machines in a LAN, an intranet, an extranet, or the Internet. While only a single device is illustrated, the term "device" shall also be taken to include any collection of devices that individually or jointly execute a set (or multiple sets) of instructions to perform any one or more of the methodologies discussed herein. The computer system 170 may be a circuit or circuits included in an electronic board card, such as a printed circuit board (PCB), a server, a personal computer, a desktop computer, a laptop computer, a personal digital assistant (PDA), a computing pad, a mobile device, or any other device, and may represent, for example, a server or a user's computer.

The computer system 170 in this embodiment includes a processing device or processor 172, a main memory 174 (e.g., read-only memory (ROM), flash memory, dynamic random access memory (DRAM), such as synchronous DRAM (SDRAM), etc.), and a static memory 176 (e.g., flash memory, static random access memory (SRAM), etc.), which may communicate with each other via a data bus 178. Alternatively, the processing device 172 may be connected to the main memory 174 and/or static memory 176 directly or via some other connectivity means. The processing device 172 may be a controller, and the main memory 174 or static memory 176 may be any type of memory.

The processing device 172 represents one or more general-purpose processing devices, such as a microprocessor, central processing unit, or the like. More particularly, the processing device 172 may be a complex instruction set computing (CISC) microprocessor, a reduced instruction set computing (RISC) microprocessor, a very long instruction word (VLIW) microprocessor, a processor implementing other instruction sets, or other processors implementing a combination of instruction sets. The processing device 172 is configured to execute processing logic in instructions for performing the operations and steps discussed herein.

The computer system 170 may further include a network interface device 180. The computer system 170 also may or may not include an input 182, configured to receive input and selections to be communicated to the computer system 170 when executing instructions. The computer system 170 also may or may not include an output 184, including but not limited to a display, a video display unit (e.g., a liquid crystal display (LCD) or a cathode ray tube (CRT)), an alphanumeric input device (e.g., a keyboard), and/or a cursor control device (e.g., a mouse).

The computer system 170 may or may not include a data storage device that includes instructions 186 stored in a computer readable medium 188. The instructions 186 may also reside, completely or at least partially, within the main memory 174 and/or within the processing device 172 during execution thereof by the computer system 170, with the main memory 174 and the processing device 172 also constituting computer readable medium. The instructions 186 may further be transmitted or received over a network 190 via the network interface device 180.

While the computer readable medium 188 is shown in FIG. 23 to be a single medium, the term "computer readable medium" should be taken to include a single medium or multiple media (e.g., a centralized or distributed database, and/or associated caches and servers) that store the one or more sets of instructions. The term "computer readable medium" shall also be taken to include any medium that is capable of storing, encoding, or carrying a set of instructions for execution by the processing device and that causes the processing device to perform any one or more of the methodologies of the embodiments disclosed herein. The term "computer readable medium" shall accordingly be taken to include, but not be limited to, solid-state memories, optical medium, and magnetic medium.

The embodiments disclosed herein include various steps. The steps of the embodiments disclosed herein may be formed by hardware components or may be embodied in machine-executable instructions, which may be used to cause a general-purpose or special-purpose processor programmed with the instructions to perform the steps. Alternatively, the steps may be performed by a combination of hardware and software.

The embodiments disclosed herein may be provided as a computer program product, or software, that may include a machine-readable medium (or computer readable medium) having stored thereon instructions which may be used to program a computer system (or other electronic devices) to perform a process according to the embodiments disclosed herein. A machine-readable medium includes any mechanism for storing or transmitting information in a form readable by a machine (e.g., a computer). For example, a machine-readable medium includes: a machine-readable storage medium (e.g., ROM, random access memory ("RAM"), a magnetic disk storage medium, an optical storage medium, flash memory devices, etc.); and the like.

Unless specifically stated otherwise and as apparent from the previous discussion, it is appreciated that throughout the description, discussions utilizing terms such as "processing," "computing," "determining," "displaying," or the like, refer to the action and processes of a computer system, or a similar electronic computing device, that manipulates and transforms data and memories represented as physical (electronic) quantities within the computer system's registers into other data similarly represented as physical quantities within the computer system memories or registers or other such information storage, transmission, or display devices.

The algorithms and displays presented herein are not inherently related to any particular computer or other apparatus. Various systems may be used with programs in accordance with the teachings herein, or it may prove convenient to construct more specialized apparatuses to perform the required method steps. The required structure for a variety of these systems is disclosed in the description above. In addition, the embodiments described herein are not described with reference to any particular programming language. It will be appreciated that a variety of programming languages may be used to implement the teachings of the embodiments as described herein.

Those of skill in the art will further appreciate that the various illustrative logical blocks, modules, circuits, and algorithms described in connection with the embodiments disclosed herein may be implemented as electronic hardware, instructions stored in memory or in another computer readable medium and executed by a processor or other processing device, or combinations of both. The components of the distributed AFI tracking system described herein may be employed in any circuit, hardware component, integrated circuit (IC), or IC chip, as examples. Memory disclosed herein may be any type and size of memory and may be configured to store any type of information desired. To clearly illustrate this interchangeability, various illustrative components, blocks, modules, circuits, and steps have been described above generally in terms of their functionality. How such functionality is implemented depends on the particular application, design choices, and/or design constraints imposed on the overall system. Skilled artisans may implement the described functionality in varying ways for each particular application, but such implementation decisions should not be interpreted as causing a departure from the scope of the present embodiments.

The various illustrative logical blocks, modules, and circuits described in connection with the embodiments disclosed herein may be implemented or performed with a processor, a Digital Signal Processor (DSP), an Application Specific Integrated Circuit (ASIC), a Field Programmable Gate Array (FPGA), or other programmable logic device, a discrete gate or transistor logic, discrete hardware components, or any combination thereof designed to perform the functions described herein. Furthermore, a controller may be a processor. A processor may be a microprocessor, but in the alternative, the processor may be any conventional processor, controller, microcontroller, or state machine. A processor may also be implemented as a combination of computing devices (e.g., a combination of a DSP and a microprocessor, a plurality of microprocessors, one or more microprocessors in conjunction with a DSP core, or any other such configuration).

The embodiments disclosed herein may be embodied in hardware and in instructions that are stored in hardware, and may reside, for example, in RAM, flash memory, ROM, Electrically Programmable ROM (EPROM), Electrically Erasable Programmable ROM (EEPROM), registers, a hard disk, a removable disk, a CD-ROM, or any other form of computer readable medium known in the art. A storage medium is coupled to the processor such that the processor can read information from, and write information to, the storage medium. In the alternative, the storage medium may be integral to the processor. The processor and the storage medium may reside in an ASIC. The ASIC may reside in a remote station. In the alternative, the processor and the storage medium may reside as discrete components in a remote station, base station, or server.

It is also noted that the operational steps described in any of the embodiments herein are described to provide examples and discussion. The operations described may be performed in numerous different sequences other than the illustrated sequences. Furthermore, operations described in a single operational step may actually be performed in a number of different steps. Additionally, one or more operational steps discussed in the embodiments may be combined. Those of skill in the art will also understand that information and signals may be represented using any of a variety of technologies and techniques. For example, data, instructions, commands, information, signals, bits, symbols, and chips, which may be referenced throughout the above description, may be represented by voltages, currents, electromagnetic waves, magnetic fields, particles, optical fields, or any combination thereof.

Unless otherwise expressly stated, it is in no way intended that any method set forth herein be construed as requiring that its steps be performed in a specific order. Accordingly, where a method claim does not actually recite an order to be followed by its steps, or it is not otherwise specifically stated in the claims or descriptions that the steps are to be limited to a specific order, it is in no way intended that any particular order be inferred.

Those skilled in the art will recognize improvements and modifications to the preferred embodiments of the present disclosure. All such improvements and modifications are considered within the scope of the concepts disclosed herein and the claims that follow.

What is claimed is:

1. A method for configuring operation of a bulk acoustic wave (BAW) resonator, the method comprising:
   determining an initial phase in a response of the BAW resonator where temperature coefficient of frequency is substantially equal to zero;
   comparing (i) sensitivity of the BAW resonator for a phenomenon of interest at the initial phase to (ii) a limit of detection threshold for the phenomenon of interest for the BAW resonator; and
   selecting a phase of the BAW resonator to be monitored as a function of time, wherein said selecting of a phase is responsive to comparison of sensitivity of the BAW resonator to the phenomenon of interest at at least one phase to the limit of detection threshold.

2. The method of claim 1, further comprising determining sensitivity of the BAW resonator for the phenomenon of interest at the initial phase prior to the comparing of sensitivity of the BAW resonator.

3. The method of claim 1, wherein if sensitivity of the BAW resonator for the phenomenon of interest at the initial phase is greater than or equal to the limit of detection threshold for the phenomenon of interest, then the selecting of a phase of the BAW resonator comprises selecting the initial phase.

4. The method of claim 1, wherein if sensitivity of the BAW resonator at the initial phase is less than the limit of detection threshold, then the method further comprises:
   determining sensitivity of the BAW resonator for the phenomenon of interest at an alternative phase; and
   comparing sensitivity of the BAW resonator for the phenomenon of interest at the alternative phase to the limit of detection threshold for the phenomenon of interest for the BAW resonator;
   wherein if sensitivity of the BAW resonator at the alternative phase is greater than or equal to the limit of detection threshold, then the selecting of a phase of the BAW resonator comprises selecting the alternative phase.

5. The method of claim 4, wherein the alternative phase comprises a more negative angle than the initial phase.

6. The method of claim 1, wherein the phenomenon of interest comprises pressure in an environment containing an active region of the BAW resonator.

7. The method of claim 1, wherein the phenomenon of interest comprises binding of mass to an active region of the BAW resonator.

8. The method of claim 1, wherein the phenomenon of interest comprises density of a fluid medium contacting an active region of the BAW resonator.

9. The method of claim 1, wherein the phenomenon of interest comprises viscosity of a fluid medium contacting an active region of the BAW resonator.

10. The method of claim 4, further comprising configuring a temperature compensation scheme to be applied to at least one output signal of the BAW resonator when the alternative phase of the BAW resonator is monitored as a function of time.

11. The method of claim 10, wherein the temperature compensation scheme comprises:
    obtaining a raw S-parameter response signal from the BAW resonator, wherein the raw S-parameter response signal includes a first phase of measurement and a second phase of measurement; and
    temperature correcting the raw S-parameter response signal, wherein the temperature correction utilizes a functional relationship between (i) a first change in frequency of the BAW resonator at the first phase of measurement and (ii) a second change in frequency of the BAW resonator at the second phase of measurement, wherein the second change in frequency is correlated to temperature, and wherein the temperature correction does not require use of a temperature signal.

12. The method of claim 2, wherein at least one of (i) the determining of the initial phase in the response of the BAW resonator where temperature coefficient of frequency is substantially equal to zero or (ii) the determining of sensitivity of the BAW resonator at the initial phase, is performed empirically utilizing a BAW resonator.

13. The method of claim 1, further comprising:
    selecting an AC signal to be supplied to the BAW resonator; and
    configuring a memory to store and/or display an output signal comprising frequency data at a phase of the BAW resonator selected to be monitored.

14. The method of claim 1, further comprising supplying a fluid containing an analyte to a fluidic passage of a fluidic device containing an active region of the BAW resonator, wherein at least one functionalization material is arranged over at least a portion of the active region, and said supplying is configured to cause at least some of the analyte to bind to the at least one functionalization material.

15. The method of claim 14, wherein the BAW resonator comprises a piezoelectric material including a c-axis having an orientation distribution that is predominantly non-parallel to normal of a face of a substrate.

16. The method of claim 14, further comprising supplying an AC signal to the BAW resonator to induce a bulk acoustic wave in the active region, and sensing at least one of an amplitude-magnitude property, a frequency property, or a phase property of the BAW resonator to indicate at least one of presence or quantity of analyte bound to the at least one functionalization material.

17. A non-transitory computer readable medium containing program instructions for execution by at least one processor of a computer system to cause the computer system to perform the following steps:
   determining, by the computer system, an initial phase in a response of a bulk acoustic wave (BAW) resonator where temperature coefficient of frequency is substantially equal to zero;
   comparing, by the computer system, (i) sensitivity of the BAW resonator for a phenomenon of interest at the initial phase to (ii) a limit of detection threshold for the phenomenon of interest for the BAW resonator; and
   selecting, by the computer system, a phase of the BAW resonator to be monitored as a function of time, wherein said selecting of a phase is responsive to comparison of sensitivity of the BAW resonator for the phenomenon of interest during at least one phase to the limit of detection threshold.

* * * * *